(12) United States Patent
Le et al.

(10) Patent No.: US 8,741,631 B2
(45) Date of Patent: Jun. 3, 2014

(54) SUBMERGED PERFUSION BIOREACTOR

(75) Inventors: Dang Quang Svend Le, Aarhus C (DK);
Jens Vinge Nygaard, Hjortshøj (DK);
Morten Foss, Skanderborg (DK);
Flemming Besenbacher, Aarhus V (DK); Cody Bünger, Auning (DK)

(73) Assignees: Aarhus Universitet, Aarhus C (DK);
Region Midtjylland, Aarhus C (DK)

( * ) Notice: Subject to any disclaimer, the term of this patent is extended or adjusted under 35 U.S.C. 154(b) by 0 days.

(21) Appl. No.: 13/375,785

(22) PCT Filed: Jun. 3, 2010

(86) PCT No.: PCT/DK2010/050125
§ 371 (c)(1),
(2), (4) Date: Mar. 19, 2012

(87) PCT Pub. No.: WO2010/139337
PCT Pub. Date: Dec. 9, 2010

(65) Prior Publication Data
US 2012/0171718 A1 Jul. 5, 2012

(30) Foreign Application Priority Data
Jun. 3, 2009 (DK) .................. 2009 00692

(51) Int. Cl.
*C12M 1/00* (2006.01)
*C12M 1/02* (2006.01)
*B01F 13/08* (2006.01)
*C12M 3/04* (2006.01)
*C12M 1/06* (2006.01)

(52) U.S. Cl.
CPC ............... *C12M 29/10* (2013.01); *C12M 27/10* (2013.01); *B01F 13/0827* (2013.01); *C12M 27/00* (2013.01); *C12M 27/02* (2013.01); *B01F 13/08* (2013.01)
USPC .................. 435/287.2; 435/287.3; 435/287.7; 435/288.3; 435/299.1; 366/274; 366/273; 366/279; 366/315

(58) Field of Classification Search
CPC ...... C12M 29/10; C12M 27/10; C12M 27/00; C12M 27/02; C12M 29/00; B01F 13/0827; B01F 13/08
See application file for complete search history.

(56) References Cited

U.S. PATENT DOCUMENTS 5,001,463 A * 3/1991 Hamburger .................. 340/627
5,705,390 A * 1/1998 Kadouri et al. ............... 435/395
(Continued)

FOREIGN PATENT DOCUMENTS

| EP | 1736536 | 12/2006 |
|---|---|---|
| WO | 99/25463 | 5/1999 |
| WO | 00/78920 | 12/2000 |

OTHER PUBLICATIONS

Orchard Supply Hardware, Melnor Ornamental Multi Pattern Sprinkler, accessed Dec. 10, 2012 online at: www.osh.com/eng/product/melnor_ornamental_multi_pattern_sprinkler/6806673.*
(Continued)

*Primary Examiner* — Nathan Bowers
(74) *Attorney, Agent, or Firm* — James Creighton Wray

(57) ABSTRACT

A device for biological purposes such as cell culturing, enzymatic reactions or filtering of fluid has a body with first and second surfaces. The body is delimited by a rim and an aperture in the center of the body. The aperture is covered at the first and second surface by first and second plates. The first and/or second plate has an inlet orifice allowing liquid medium into the aperture. Rotating means are arranged in the aperture between the first and second plate. At least one recessed portion is a cavity in the rim of the body having a first outlet orifice allowing the liquid medium to flow out of the body. At least one outlet channel connects the circular aperture with the recessed portion. Liquid is pumped into the aperture of the device and pumped through at least one outlet channel.

42 Claims, 14 Drawing Sheets

(56) References Cited

U.S. PATENT DOCUMENTS

| | | | | |
|---|---|---|---|---|
| 6,660,509 | B1 | 12/2003 | Herman | |
| 7,152,814 | B1* | 12/2006 | Schapper et al. | 239/520 |
| 2002/0160506 | A1* | 10/2002 | VanErdewyk | 435/304.1 |
| 2002/0197197 | A1* | 12/2002 | Green | 422/261 |
| 2004/0147015 | A1 | 7/2004 | El-Haj et al. | |
| 2007/0082390 | A1* | 4/2007 | Hastings et al. | 435/305.2 |
| 2007/0189115 | A1* | 8/2007 | Yaniv et al. | 366/274 |
| 2009/0024229 | A1* | 1/2009 | Chen et al. | 623/23.73 |
| 2011/0203995 | A1* | 8/2011 | Persson et al. | 210/683 |

OTHER PUBLICATIONS

3D Biotek, LLC., "3D Culturing is Superior to 2D Conventional Culturing in Examining The Osteogenic Potential of Stem Cells In Vitro" attached, publication date unknown, after 2008.
Fennell, "Investigation into the Accessibility of Clasps" www.tiresias.org/research/reports/clasps.html, 2007, retrieved Dec. 12, 2011.
Abbott, "Cell Culture: Biology's new dimension" Nature 424, 870-872, Aug. 21, 2003, doi:10.1038/424870a.
Anders et al., "Disruption of 3D tissue integrity facilitates adenovirus infection by deregulating the coxsackievirus and adenovirus receptor" PNAS 2003 100 (4) 1943-1948; published ahead of print Feb. 7, 2003, doi:10.1073/pnas.0337599100.
Willerth et al, "Optimization of fibrin scaffolds for differentiation of murine embryonic stem cells into neural lineage cells" Biomaterials, 27:5990-6003, 2006.
Machado et al, "3D chitosan-gelatin-chondroitin porous scaffold improves osteogenic differentiation of mesenchymal stem cells" Biomed. Mater. 2:124-131(2007).
Grayson et al, "Human Mesenchymal Stem Cells Tissue Development in 3D PET Matrices" Biotechnol. Prog. 20 (3):905-12 (2004).
Ko et al, "Engineering Thick Tissues—The Vascularisation Problem" European Cells and Materials 14:1-19 (2007).
Cartmell et al., "Effects of Medium Perfusion Rate on Cell-Seeded Three-Dimensional Bone Constructs in Vitro" Tissue Engineering. Dec. 2003, 9(6): 1197-1203. doi:10.1089/10763270360728107.
Bancroft et al, "Technical Note: Design of a Flow Perfusion Bioreactor System for Bone Tissue-Engineering Applications" Tissue Engineering. Jun. 2003, 9(3): 549-554. doi:10.1089/107632703322066723.
Timmins et al, "Three-Dimensional Cell Culture and Tissue Engineering in a T-CUP (Tissue Culture Under Perfusion)" Tissue Engineering. Aug. 2007, 13(8): 2021-2028. doi:10.1089/ten.2006.0158.
Angele et al, "Cyclic hydrostatic pressure enhances the chondrogenic phenotype of human mesenchymal progenitor cells differentiated in vitro" Journal of Orthopaedic Research 21(3): 451-457, May 2003.
Robinson, "The Responses of Cells to Electrical Fields: A Review" The Journal of Cell Biology, 101(6): 2023 (1985).
Sauer et al., "Effects of electrical fields on cardiomyocyte differentiation of embryonic stem cells" Journal of Cellular Biochemistry 75(4): 710-723, Dec. 15, 1999.
Chen et al., "Estimation of Central Aortic Pressure Waveform by Mathematical Transformation of Radial Tonometry Pressure: Validation of Generalized Transfer Function" Circulation 95:1827-1836 (1997).
Klibanov, "Immobilized enzymes and cells as practical catalysts", Science 219:722-7 (1983).
Janne L. Simonsen et al., Telomerase Expression Extends the Proliferative Life-Span and Maintains the Osteogenic Potential of Human Bone Marrow Stromal Cells, Nature Biotechnology, Jun. 2002, 592-596, vol. 20, Nature Publishing Group.

* cited by examiner

A  B

A       B

SUBMERGED PERFUSION BIOREACTOR

This application claims the benefit of Danish Application No. PA 2009 00692 filed Jun. 3, 2009 and PCT/DK2010/050125 filed Jun. 3, 2010, International Publication Number WO 2010/139337 A1, which are hereby incorporated by reference in their entirety as if fully set forth herein.

FIELD OF THE INVENTION

The present invention relates to a device for obtaining a perfusion flow e.g. for culturing of cells, especially, the culturing of cells in three-dimensional structures. Furthermore, a method for culturing cells and in particular culturing cells in three-dimensional structures is provided. This invention also relates to the use of a device for culturing of cells for the purpose of tissue engineering and artificial organs.

BACKGROUND OF THE INVENTION

The culturing of cells is a highly complex matter as different cell types demand different types of liquid medium as well as different growth conditions in order to obtain optimal growth of the cells. The growth conditions include chemical composition and flow rate of the medium, mechanical stimulation, and electromagnetic stimulation.

Cells can be cultured in 2D (dimensional) layers and have traditionally been cultured in culture tissue flasks and culture plates. In this manner, the cells are grown in a monolayer where the liquid medium is added on top of the cells. The culture flasks and dishes are placed inside an incubator in order to optimise the temperature and $CO_2$ level. However, monolayer cultures are not optimal for cells as they do not experience conditions similar to their natural environment. In order to obtain a more natural environment for the cells, changes in the growth conditions can be induced as for example, changes of the oxygen level.

It has been shown through numerous experiments that in most cases 3D cell cultures mimic the in vivo situation much closer than 2D cell cultures, especially concerning primary cells. The main reason is that the natural environment typically is 3D. Therefore, 3D cell cultures represent an important field for modelling/controlling the complex biological processes in vitro There is a big difference between a flat layer of cells and a complex, 3D tissue (Abbott A, "Biology's new dimension", Nature 21:870-872, (2003). For example, in 2D cultures, both normal and malignant mammary epithelial cells have similar, high levels of Coxsackievirus and adenovirus receptors (CAR). But in 3D cultures, only malignant cells have an upregulation of CAR (Anders M et al. Proc. Natl. Acad. Sci. USA 100, 1943-1948, (2003).

Furthermore, cell culture experiments with embryonic stem (ES) cell proliferation and differentiation in 3D scaffolds also show a greater cell proliferation and differentiation than 2D cultures (Willerth S M, et al., "Optimization of fibrin scaffolds for differentiation of murine embryonic stem cells into neural lineage cells", Biomaterials, 27:5990-6003, (2006).

For adult stem cells such as human mesenchymal stem cells (hMSCs), 3D culturing has proven to be superior to 2D conventional culturing in relation to the osteogenic potential of stem cells in vitro (Machado C B et al., "3D chitosan-gelatin-chondroitin porous scaffold improves osteogenic differentiation of mesenchymal stem cells", Biomed. Mater. 2:124-131, (2007); Grayson W L et al., "Human mesenchymal stem cells tissue development in 3D PET matrices", Biotechnol Prog., 20(3):905-12, (2004); 3D Culturing is Superior to 2D Conventional Culturing in Examining The Osteogenic Potential of Stem Cells In Vitro, 3D Biotek, LLC, North Brunswick, N.J., 675 US Highway 1, North Brunswick, N.J. 08902, http://3dbiotek.com/Documents/3DScaffold_Osteogenesis.pdf.).

Even if the differentiation is successful in 2D the usage in clinical applications has been limited, because the architecture of the formed extracellular matrix is diverse from the native tissue morphology.

In order to obtain proper differentiated cells which can be used for tissue engineering purposes, different 3D culturing processes with the use of porous scaffolds have been developed.

3D cultures require means of increasing the flow of nutrients and oxygen to the cells and removal of waste products from the cells situated centrally in the scaffold, as simple diffusion is insufficient for transport at distances longer than approx. 200 µm (Ko HCH et al., "Engineering thick tissues—the vascularisation problem", European Cells and Materials, 14:1-19, (2007).

Sufficient transport to the centre of the scaffold can be achieved by spinning the cells in flasks—so called spinner flasks—as described for example in EP 1 736 536 A2. The cells are adherent to scaffolds which are then arranged in spinner flasks filled with liquid medium. The medium is set in motion relative to the scaffolds with a magnetic stirrer bar or a shafted impeller to provide a convective means to enhance nutrient/waste exchange to and from the fixed scaffold. This fluid motion effects increased shear on the adherent cells, which is known to influence cell differentiation.

The main drawback of this culture method is that the scaffolds are not thoroughly or evenly perfused. Furthermore, because the viscous flow field around each scaffold is dependent on the exact spatial position in the flask, it is difficult to achieve consistent results when culturing more than 8 samples in one flask. This is a disadvantage of this method, as it increases the overall footprint of the perfusion setup.

The increased mass transport due to convection is limited to a volume near the surface of the scaffolds. The interior of the scaffold is still reliant on diffusion. As for the effects of increased shear stress on the differentiation of the cells, these are also confined to the cells located superficially in the scaffold.

Other methods comprises perfusion flow where small scaffolds can be situated at the bottom of culture racks and liquid medium is directed across the scaffolds in order to supply the nutrients in a continuous manner (Cartmell S H et al., "Effects of Medium Perfusion Rate on Cell-Seeded Three-Dimensional Bone Constructs in Vitro",. Tissue Engineering, 9(6): 1197-1203, (2003); Bancroft G N et al., "Technical Note: Design of a Flow Perfusion Bioreactor System for Bone Tissue-Engineering Applications", Tissue Engineering, 9(3): 549-554, (2003)). However, these methods have huge drawbacks. For the perfusion flow, the equipment itself is not ideal since a large amount of tubes are needed in order to sustain a constant flow of liquid medium. Furthermore, a large amount of equipment like pumps and flasks are arranged inside the incubator, thus taking up large amounts of valuable incubator shelf space.

Another method of perfusing scaffolds is to mount the scaffolds on a micro-controlled linearly actuated plunger, which then moves reciprocally up and down within a medium containing vessel (Timmins N E et al., "Three-Dimensional Cell Culture and Tissue Engineering in a T-CUP (Tissue Culture Under Perfusion)", Tissue Engineering, 13(8):2021-2028, (2007). This system fails to eliminate the need for tubing and comprises a large number of assembly parts. Furthermore, although the mean flow through the scaffold can be calculated, non-uniformity between individual scaffolds will lead to non-uniform perfusion.

OBJECT OF THE INVENTION

It is the object of the present invention to create a cell culture method which reduces the above mentioned problems. Thus, it is the purpose of this invention to create a compact device which is simple in setup without the need of external pumping mechanisms in order to obtain a perfusion flow system.

DESCRIPTION OF THE INVENTION

This invention addresses these problems by providing a device for biological purposes such as cell culturing, enzymatic reactions or filtering of fluid where the device comprises

- a body having a first and a second surface defining a body thickness there between, and where said body is delimited by a rim;
- an aperture in the centre of the body; said aperture is covered at the first and second surface by a first and second plate, where the first and/or second plate comprises an inlet orifice allowing liquid medium into the aperture;
- means for rotating; said means for rotating is arranged in the aperture between the first and second plate
- said rim comprises at least one recessed portion for cell culturing; said recessed portion is a cavity in the rim of the body comprising a first outlet orifice allowing the liquid medium to flow out of the body; and a first wall delimiting said recessed portion along said cavity;
- at least one outlet channel connecting the circular aperture with the recessed portion for cell culturing.

The body and the aperture of the body according to this invention are preferably in a circular shape. However, other shapes may also be an advantage if an uneven liquid flow across recessed portion is desired.

Throughout the manuscript cell or cells is a common denominator for all micro- and mesoscopic biological units: prokaryotic, eukaryotic cells, protozoa, larvae, worms and the eggs of these. Furthermore, same term applies for cells that have undergone encapsulation, aggregation etc.

One device can contain one or more recessed portions. The recessed portions are connected with an aperture in the body through an outlet channel. Liquid medium enters the aperture of the body through an inlet orifice present in the first and/or second plate, flows through the outlet channels and the recessed portions before it is allowed to flow out of the body by the first outlet orifice.

The inlet orifice is present in a first plate that is arranged on one side of the aperture while a second plate is arranged on the other side of the aperture to prevent liquid medium to flow through the aperture. Optionally, in order to obtain an optimal flow the cross-sectional area of the inlet orifice can be considerably smaller than the cross-sectional area of the aperture but larger than the cross-sectional area of the outlet channel where it is connected to the aperture.

The device can be made of polysulfone, polytetrafluoroethylene, polystyrene, polyethylene, polypropylene, or other similar materials which are ordinarily used purposes. Additional materials, which can be used for the device, are injection mouldable ceramics or composites. Different parts of the device can be made from different types of materials e.g. the body can be made from polysulfone while the means for rotation can be made of Teflon®.

Additionally, the device can be made of a biodegradable material. Hereby, the cultured cells with or without a scaffold can remain in the device or part of the device at implantation. The recessed portion is left inside the person or animal but will undergo controlled degradation.

As an alternative, the surfaces of the recessed portions can be modified where the cells are to be cultured. This can be performed in a traditional way as used for cell culture flasks or as reported in the literature in order for the cells to attach directly to the recessed portion. In this way, one is able to grow cells directly in the recessed portion as well as in different types of scaffolds. Furthermore, the surfaces can be treated not only to induce attachment of cells but also to affect the cells and promote their proliferation or differentiation. As an example growth factors and/or hormones can be reversibly bound to the surface directly or through a coating, and affect the cells during culturing with or without the scaffolds.

In an advantageous embodiment, the device for biological purposes such as cell culturing, enzymatic reactions or filtering of fluid further comprises means for reliably centring and levelling the device in a liquid medium containing vessel.

In order to obtain a uniform flow, the device needs to be centred and leveled in a stationary position with regard to the vessel. This can be performed for example by adding a small fastener to the device, which is capable of positioning the device inside the vessel and avoiding it to be displaced with regard to e.g. a magnetic field. This can either be performed by placing at least two fasteners opposite one another between the body of the device and the sides of the liquid medium containing vessel. Alternatively, one or more fasteners can be arranged between the body of the device and the bottom of the liquid medium containing vessel i.e. keeping the body in place with regard to for example a magnetic field but still allowing it to freely rotate.

Furthermore, it is presumed that if the means for rotating consists of a magnet, which is activated by a magnetic stirrer to be arranged below the liquid medium containing vessel and thus the device, the magnetic field created by the magnetic stirrer can be of a strength, which automatically arranges the magnet in the centre of the aperture.

Hereby, the device is kept at the same position with regard to the magnetic field and the unity of the flow in the different channels is not disturbed.

The term liquid medium containing vessel is here to be understood as any beaker, box, flask, plate, pot and the like, which can be used in relation to the device in order for the invention to function properly.

Throughout the description the term rim is to be understood as the outer edge of the body. The rim can be a firm rim between the first outlet orifices of the body and the first and second surface or it can be partly open.

The surfaces can either be plane surfaces covering the, in use, top and bottom of the body or the surfaces can be integrated at least partially with the parts of the outlet channels and recessed portions. Integrating the first and second wall at least partly with parts of said first wall of at least one recessed portion and parts of said outlet channel results in that the shape of the outlet channel along with the shape of the recessed portion is part of the shape of the surface and thus, result in that the shape of the surface is not plane.

In an advantageous embodiment, said first and second surfaces are essentially parallel, which provides the body of the device with an even thickness along the body.

In an advantageous embodiment the first plate and/or the second plate is an integrated part of the device.

The aperture of the device is covered on both sides by plates. One of the plates contains an inlet orifice in order for the liquid medium to enter the device. These plates can be an integrated part of the cell device. Hereby, the risk of contamination of the cell culture device is diminished since multiple parts create multiple grooves which enhance the possible growth of e.g. fungus or bacteria.

In another advantageous embodiment, the device for biological purposes such as cell culturing, enzymatic reactions or filtering of fluid is an integrated part of a vessel. This further decreases the number of parts to be handled and combined since the device is not to be placed into a vessel before liquid medium is added. In a further advantageous embodiment, a lid is provided with the vessel to be arranged over the opening of the vessel after scaffolds or cells have been arranged into the device and liquid medium has been poured into the vessel. Decreasing the number of the parts to be combined and further arranging a lid over the opening of the vessel decreases the risk of contamination.

The term vessel is to be understood as any vessel, container, Petri dish, beaker, bottle etc., which is able to contain liquid medium and cover a device lowered into the liquid medium in order for liquid medium to be pumped into the liquid orifice of the device.

In a further advantageous embodiment, the device for biological purposes such as cell culturing, enzymatic reactions or filtering of fluid is divided into two parts, a top part and a bottom part, along a plane substantially parallel to said first or second plate, and where said plane further divides said at least one recessed portion and said at least one outlet channel.

The invention further describes a device for biological purposes such as cell culturing, enzymatic reactions or filtering of fluid where the device comprises two parts a bottom part and a top part, where said bottom part and said top part can be assembled into a body said top part comprises a first surface, a first aperture in the first surface; said first aperture being covered by a first plate, where the first plate comprises an inlet orifice allowing liquid medium into the aperture;

an upper part of a tunnel-shaped section constituting part of a recessed portion, where said tunnel-shaped section is arranged extending inwards from the edge of said top part;

an upper part of at least one outlet channel connecting the first aperture with said at least one recessed portion;

said bottom part comprises a second surface, a second aperture in said second surface; said second aperture being covered by a second plate;

a lower part of at least one recessed portion corresponding in size and shape to said recessed portion in said upper part;

a lower part of at least one outlet channel connecting the second aperture with said at least one recessed portion where said top part and said bottom part comprises means for being assembled, whereby the lower part of said at least one recessed portion is superposed with said upper part of said at least one recessed portion and said lower part of said at least one outlet channel is superposed with said upper part of said at least one outlet channel, and where said first and second aperture are superposed forming one aperture, and means for rotating are arranged in the aperture.

In a further advantageous embodiment, the bottom part is integrated in a vessel.

In this embodiment, the device comprises two parts—a bottom part and a top part. The two parts can be formed by dividing the device along a plane arranged between the first and second surface of the body of the device, i.e. the plane penetrates the rim of the body. Preferably, the body i.e. the thickness between the first and second surface at the first outlet orifice is divided into halves. However, the division can be made otherwise as long as cells and/or scaffolds are easily arranged in the lower part of the recessed portions.

The bottom part comprises the, in use, lower part of the recessed portions, the, in use, lower part or partially the lower part of the outlet channels, the second surface, the second plate, and the, in use, lower part of the aperture, into which the means for rotating optionally, can be arranged. As an advantageous embodiment, the bottom part of the device is integrated into the floor of a vessel and thus, is integrated with the vessel as previously described.

The top part comprises the, in use, upper part of the recessed portions, the, in use, upper part or partially the upper part of the outlet channels, the first surface, the first plate, the inlet orifice, and the, in use, upper part of the aperture.

The upper part of the recessed portions is tunnel-shaped sections arranged to extend inwards from the edge of said top part. In addition, the lower part of the recessed portions is tunnel-shaped sections arranged to extend inwards from the edge of said bottom part. This tunnel-shaped section from the top part corresponds to the size and shape of the lower part in the bottom part, whereby a recessed portion is formed by superposing the upper part and lower part of the tunnel-shaped sections. The formed recessed portion forms a first outlet orifice at the rim of the body defined by and/or between the edges of the top and bottom part.

The size and shape of the tunnel-shaped section thus defines the size and shape of the recessed portion. It is implicitly to be understood that the size and shape of the recessed portion only has to correspond in a manner such that the assembling of the top part and the bottom part forms a smooth crossing from the upper part to the lower part of the recessed portions.

Assembling of the bottom part and the top part, thus results in a body with a first and second surface comprising an aperture superposed from the first aperture and the second aperture, where the aperture is covered by a first plate and a second plate. Liquid is pumped through an inlet orifice present in the first plate and into the aperture by means of rotating. The body further comprises at least one outlet channels formed by the superposing of an upper part and a lower part from the top part and bottom part, respectively. In addition, the body comprises at least one recessed portion formed by the superposing of an upper tunnel-shaped section forming the upper part of the recessed portion and a lower tunnel-shaped section forming the lower part of the recessed portion. The so formed outlet channel fluidly connects the aperture with the recessed portion, and the liquid can leave the body through the first outlet orifice formed by the tunnel-formed sections.

The first plate and/or the second plate can be an integrated part of the body or they can be attached to the parts. In an advantageous embodiment the inlet orifice can be a small tube through which the liquid is pumped into the aperture. Adding a small tube to the top part lighten the handling of the top part during the assembling process.

In an advantageous embodiment, the bottom part and top part comprise means for assembling the parts to one another in a manner that enables the two parts to be secured even during rotation. These means could be: snap locks, magnetic locks, screws and threads, press-fittings and/or protrusions engaging into openings when assembling the two parts. The number of means present on each device is to be sufficient in order to keep the two parts together during rotation. Thus, multiple means are to be present if the speed is high and the engagement is only superficial, while only a few means or one means is to be present in case of a tight fitting of each means. As an alternative the two parts could be combined by other methods such as using gluing or welding the parts together.

Advantageously, the means can be opened and closed multiple times, in order to allow access to the cells and/or scaffolds during the experiment and to be able to re-use the device multiple times.

The two-parted device i.e. comprising a bottom part and a top part is used in the following way. Scaffolds and/or cells are arranged into the recessed portions of the bottom part and the means of rotation is arranged in the lower part of the aperture. Hereafter, the top part of the device is assembled with the bottom part. The assembled device can then be arranged in a vessel if the bottom part is not an integrated part of a vessel or if the bottom part was not arranged in the vessel before the scaffolds were arranged herein. Liquid medium is poured into the vessel until it more than covers the device whereafter rotation is started and the liquid can pass through the inlet orifice and pass the cells and/or scaffolds.

As an alternative, the means for rotating can be arranged after the assembling of the bottom part and the top part if the first or second plate are not integrated in the top part and bottom part, respectively.

The two-parted device provides easy access to the recessed portions and the aperture for placing and removing the cells/scaffolds and the means for rotating. This makes the handling of the device easier and quicker, and thus, decreases the risk for contamination. Furthermore, this embodiment makes it easier to automate the handling process.

As a further advantageous embodiment, the device can be provided as a kit with three parts: a bottom part integrated in a vessel, a top part to be arranged on top of the bottom part and a lid to be arranged on top of the vessel.

In addition, a method for making a device for biological purposes such as cell culturing, enzymatic reactions or filtering of fluid is described where said device is made by moulding for example injection moulding or blow moulding.

The device can be made of different types of plastic along with injection mouldable ceramics or composites. Moulding is an economically beneficial way of making a top part and a bottom part, optionally along with a vessel and a lid, especially if the parts are formed from one single piece of material. Furthermore, integrating the bottom part into the vessel can be performed by moulding.

In a further advantageous embodiment the device for biological purposes such as cell culturing, enzymatic reactions or filtering of fluid further comprises an external means, where the external means engages with the recessed portions of the body where said external means or the outlet channels and comprises an inlet opening and a second outlet opening and a fluid connection between said inlet opening and said second outlet opening; said external means is a three-dimensionally shaped element delimited by a second wall defining an exterior surface of said external means.

It is an advantage to combine the device with external means. Hereby, the scaffolds containing the cells or the cells themselves can be introduced into the external device means before they are combined with the body itself. Especially for handling purposes this is highly advantageous since one would have to rotate the body and angle it in order to engage scaffolds or cells into the different recessed portions of the device.

Furthermore, the external means can be changed during the experiment by removing one external means and adding a new one. This way, one is able to perform time-resolved experiments where the cells are influenced by similar cell growth conditions.

The external means can fit by press-fit into the recessed portions. As a preferable embodiment, the external means contain a flange along the outer rim. Hereby, the external means can be inserted at a specific position in the recessed portions. Furthermore, the external means is more easily detached by means of the flange. As a further embodiment, a specific device for loosening the external means can be provided with the external means. Still, in another embodiment the device comprises external means for fixing the external means to the body.

In a further advantageous embodiment the external means comprises an outer thread where said outer thread engages with an inner thread provided in the internal means when the external means is engaged with the recessed portions.

As opposed to a press-fit connection between the external means and the recessed portions, threads can be arranged on the inside the recessed portions and on the outside of the external means. In this way, the external means is combined with the recessed portions. For the implementation in which the external means engage with the outlet channels from the central aperture, the thread of the outlet channels can be either male or female and vice versa for the external means. It may be advantageous to let said threads have the shape of Luer Lok®. This is preferred in some experiments in order for the external means and the recessed portions to be thoroughly attached to one another. In addition, the detaching and attaching of the two parts may be more reliable and easier to handle than by press-fitting.

As an alternative, the external means as well as the two parallel plates can be secured using e.g. a slide-lock clasp design or a tooth clasp design as illustrated on http://www.tiresias.org/research/reports/clasps.html.

In a further advantageous embodiment, to induce superficial shear stress on the scaffold, the external means for cell culture can be designed so as to allow flow around the perimeter of the contained scaffold. This modification to the external means for cell culture will sharply decrease the perfusion flow rate within the bulk of the scaffold. This arrangement will simulate the effects of spinner flask cultivation, but with a much higher reproducibility and with a much smaller setup footprint.

In a further advantageous embodiment the outlet channel is conically shaped, where the smallest cross sectional area of the conically shaped outlet channel is in connection with the aperture. In a still further advantageous embodiment the conical shape of the outlet channel continues in at least a part of the recessed portion and/or in at least a part of the external means; said part of the recessed portion and/or said part of the external means is in contact with the outlet channel.

By changing the shape of the outlet channel from a narrow channel with a sustained cross-sectional area to a conically shaped channel a great deal of turbulence is prevented. The outlet channel begins at the aperture as a narrow orifice and then continuously increases in size until it equals the size of the recessed portions of the cell culturing at the border between the outlet channel and the recessed portions of the cell culturing. The flow of the liquid medium experiences a gradual increase in cross-sectional area as opposed to an abrupt increase as when the device is provided with narrow channels. Thus, turbulence is prevented.

Turbulence can affect the growth pattern of the cell cultures and the cell cultures can be affected differently at different positions in the 3D culture. Hence, an uneven growth pattern can be created as well as an uneven differentiation of the cells.

The overall quality of for example a cell-seeded scaffold which is to be used for tissue engineering purposes decreases. Furthermore, reproducibility of the cell culture studies is harder to obtain.

Preferably, the conical shape continues further than the border between the recessed portions and the outlet channel. The conical shape can either continue to the first or second outlet orifice in a continuous manner or leave a part of the recessed portions before the first outlet orifice or a part of the external means before the second outlet orifice. The part left without a conical shape is to fit the size of for example a scaffold to be arranged in said recessed portions or the external means. Thus, all the way from the aperture and to the scaffold, the cross-sectional area experienced by the liquid medium is increased in a conical manner.

The shape of the aperture and the channels may be optimized in terms of flow and lower risk of air bubble entrapment during scaffold loading or intermittent resurfacing. Computational Fluid Dynamics (CFD) calculations can be performed to ascertain optimal geometry of the conical channels. Flows can also be tailored in this way for specific applications where a non-uniform flow is advantageous.

In an advantageous embodiment, the size of the inlet orifice can be regulated by engaging the inlet orifice with one or more inserts.

The low pressure created centrally by the rotating means effects the flow of liquid medium through the aperture of the body. One determining factor to the flow of the liquid medium is the size of the inlet orifice. By adjusting the size of the inlet orifice, the flow rate into the aperture is adjusted and hereby, the flow rate through the outlet channels and through the cell cultures.

The inlet orifice can be adjusted in several ways, for example by different sizes of inserts to be arranged inside the inlet orifice. As an alternative, the inlet orifice can be changed continuously by means integrated inside the inlet orifice. This could be performed by changing the inlet orifice due to a shutter mechanism whereby the inlet orifice is gradually decreased or increased. The flow rate can be adjusted during the experiment and thus more dynamic experiments can be performed in order to optimise the cellular growth.

Advantageously, the inlet aperture can comprise means for connecting external means for e.g. in-line flow measurements, central external means, or bolus media loading. Said in-line flow measuring equipment can comprise a simple inverted ultra-low flow rotameter having a float lighter than the liquid media.

In an advantageous embodiment, a large external means can be engaged with the central inlet orifice of the first parallel plate of the device body. Thus the inlet orifice becomes a low pressure sink. This arrangement will be advantageous for large scaffolds or for conditioning the liquid media prior to its distribution to the scaffolds in the peripherally located external means of cell culturing or the recessed portions. By conditioning, one may imagine a population of seeded cells that lower the oxygen tension of media or that secrete signal molecules, which are then carried off to the peripheral scaffolds to induce differentiation or proliferation.

In a further advantageous embodiment, the recessed portions and/or the external means comprises a first regulatory mechanism to regulate the size of the outlet openings.

The cellular growth and differentiation can also be adjusted by means of changing the size of the first and/or second outlet orifice. If the first and/or second outlet orifice is completely closed, no media is able to flow through the cell cultures. If only the second outlet orifice is closed the pressure level inside the body increases. Thus, an increased hydrostatic pressure is provided to the cells. The proliferation of the cells is influenced and certain cell cultures can be stimulated in this manner (Angele, P et al., "Cyclic hydrostatic pressure enhances the chondrogenic phenotype of human mesenchymal progenitor cells differentiated in vitro", Journal of Orthopaedic Research 21(3):451-7, (2003).

The pressure can be controlled by providing the first and/or second outlet orifice with the ability to be continuously or step-wise adjusted in size. This can be of huge advantage for dynamic cell culturing.

The control of the outlet orifice may be either manually or automatically by e.g. insertions with different sizes of the diameter which can be combined with the first and/or second outlet orifice or an automatic adjustment such as a shutter which can be controlled by e.g. a micro-processor. As a further embodiment, the micro-processor can further accomplish a measurement of the pressure. Hereby, certain limits of pressure can be induced where after the first and/or second outlet orifice automatically opens to decrease the pressure eventually or not until after a certain time has passed by. Then the first and/or second outlet orifice can be closed or nearly closed once again and pressure can be increased once more. Hereby, time-varying hydrostatic pressure can be provided to the cells.

Flow and hydrostatic pressure to the cells can also be regulated alone or in part simply by changing the rotational speed and or the shape of the rotating means. Example 2 illustrates by means of computational fluid dynamic how the pressure can be modulated by the shape of the rotation means.

In a further advantageous embodiment, the means for rotating is magnetic.

As a preferred form of the means for rotating, a magnet can be used. The magnet is introduced into the aperture of the body. The magnet can be rotated by placing the device on top of a magnetic stirrer.

The size and shape of the magnet can either enable it to rotate freely within the aperture of the body or possibly be affected by the inside rim of the aperture to affect the speed of rotation. The speed of rotation can as well be affected by the type of material chosen.

Although freely rotating, the size and shape of the magnet can have effects on the fluid flow experienced by the cells situated in the recessed portions or the external means. A magnetic stirrer bar, the length of which is just barely smaller than the diameter of the central aperture, will generate an intermittent flow wave through the outlet channels with a frequency two times the rotational speed. This pulsation will stimulate the cells differently than a constant flow, as cells mechanically should be regarded as being viscoelastic. A pulsatile flow should thus be able to activate pathways that lead differention. On the other hand; a smaller fast rotating magnet can produce the same flow rate through the channels, but with a higher beat frequency. Furthermore, the shape of the magnet can also be changed in different ways in order to create a pulsatile flow. One example, hereof, is illustrated in example 2.

As an alternative, different means of rotating can be provided. A modular shafted impeller can be inserted into the aperture of the device. Hereby, flow of liquid medium through the outlet channels is generated by centrifugal force.

Application-specific impellers, whether shafted or magnetic, can be designed so that the passage of the liquid medium from the aperture to each individual outlet channel is time-varying for periods of each impeller/stirrer bar revolution. Thus, an alternating pressure and hereby flow is created for the outlet channels and a periodic flow with controllable frequency through the cell cultures and/or scaffolds is obtained. This effect is advantageous for culturing e.g. MSCs for osteogenic differentiation or for culturing endothelial cells. The shape of said application-specific magnetic stirrer bar or impeller and the optimal rotation speed, by which the desired pulse shape is generated, can be determined using CFD simulations.

Furthermore, means can be provided in which not only the liquid medium is rotated in order to create low pressure but also to rotate the body.

In a further advantageous embodiment, the body comprises means for creating an electrical field.

Fields of electricity affects cells in various ways, (Robinson K R, "The response of cells to electrical fields: A review", The Journal of Cell Biology, 101:2023, (1985)) e.g. by promoting cell proliferation or differentiation (Sauer H et al., "Effects of electrical fields on cardiomyocyte differentiation of embryonic stem cells", Journal of Cellular Biochemistry, 75(4):710, (1999)). An electrical field is, thus, of advantage to some cell studies in order to promote cellular growth and differentiation, e.g. of embryonic stem cells. An electromagnetic field can be induced by introducing magnetic particles or coils in the vicinity of the recessed portions and/or the external means. In addition or alternatively, conducting material like carbon particles or electrically conducting polymers can be included in certain areas of the device.

The force of the electrical field is to be between 0.2-4 kV/m, preferably between 0.5-2 kV/m, most preferred around 1 kV/m.

In a further advantageous embodiment, the recessed portions and/or the external means comprises means for retaining a scaffold.

Culturing of cells and promoting cell proliferation and differentiation in a 3D culture is most easily performed by attaching the cells to a 3D scaffold. The scaffold can be of various types, of different materials e.g. chitosan, poly(L-lactic acid) (PLLA), poly(D; L-lactic acid) (PDLLA), poly (D,L-lactic-co-glycolic acid) (PLGA), poly(lactic acid-co-caprolactone) (PLCL), poly(glycolic acid-co-caprolactone) (PGCL), poly(byturate-co-valerate), cellulose, silk fibroin, zein, Trabecular Metal® (tantalum), titanium meshes, sintered hydroxyapatite, tricalcium phosphate, coral, or any other natural material. Any combination of the aforementioned materials can also be used. The scaffolds may have different porosity from e.g. 50% to 99%, and with a variety of elastic moduli depending on the type of cells cultured along with the tissue-type to be.

However, for all different types of scaffolds it is essential that the scaffold is not moved during the culturing e.g. because of the flow. That is the flow encounters resistance when passing through the scaffold and may push the scaffold along the flow. Thus at the worst, the scaffold is removed from the device due to the pushing of the flow. Furthermore, it is beneficial not to be able to push the scaffold too far into the recessed portion.

Possible means can be ridges or small flanges, which holds the scaffold at a given position.

The size of the scaffold to be retained is between 1 mm$^3$-1000 cm$^3$, preferably between 4 mm$^3$-1000 cm$^3$. The size and shape dependent upon the cell types to be cultured and the tissue-types to be differentiated. The scaffolds may have any geometrical shape including cubes, cuboids, cylinders, cones, triangular prisms, pyramids, regular tetrahydron.

The term scaffold is to be interpreted throughout the document as any material or composition of materials with a 3D architecture. This architecture is capable of supporting the proliferation and differentiation of cells as well as supporting the attachment of cells, proteins e.g. enzymes, carbonhydrates, RNA, DNA, lipid micelles, nanoparticles. The scaffolds may furthermore be drug delivery carriers of both biological and non-biological drugs.

Furthermore, porous scaffolds are to be considered as being filter material for particles larger than the pores.

In a further advantageous embodiment two or more devices can be stacked with their surfaces essentially parallel, and where the devices are separated by spacers, said spacers are attached to the devices. The spacers can be either integral or external to the devices or to parts of the devices (i.e. the body, the parallel plates, the inlet orifice adapter, or the external means for cell culture)

More devices can advantageously be connected by spacers between the different devices. In this manner, the means for rotating in each of the devices rotate and transport the liquid medium through the device and to the recessed portions or the external means. Hereby, it is achieved that multiple scaffolds are kept at similar conditions. The liquid medium is the same and as well as the conditions which is highly preferable to obtain reproducible experiments. Furthermore, the footprint of this expanded setup is keep at a minimum, which saves valuable incubator shelf space and expensive liquid growth medium. The spacers between the different devices may be either detachably attached, or they may be an integrated part of one device, which then connects to another device.

In a still further advantageous embodiment, the inlet orifice comprises a connective means; said connective means connects an external compartment to said inlet orifice; said external compartment comprises an indicator solution with a given concentration of indicator.

The flow rate of the liquid medium into the aperture of the device through the inlet orifice can be calculated by connecting an external compartment to the inlet orifice of the device. The external compartment is attached to the body through connective means, which is to be understood as any means that are capable of reversible joining the opening of the compartment with the inlet orifice in a way whereby leakage is avoided e.g. the entire solution inside the compartment enters the aperture of the device. In addition, the external compartment has to be made from a non-leaky material itself.

As an example of a connective means a first plate can be made comprising one or more flanges to be inserted inside the opening of the external compartment together with a collar, which can be attached and tightened to the outside of the external compartment in order to prevent leakage. In another embodiment, the external compartment is sealed by a rubber stopper, which is pierced by a large bore needle when connecting with the inlet orifice.

The external compartment comprises an indicator solution, where the indicator is provided at a given concentration. The indicator is preferably an easily measurable solute that does not cause discernible changes in media viscosity or density. Examples are fluorescent dyes, absorbent dyes, salts, acids and bases, sugars etc.

It is important that the described calibration is carried out using the scaffolds from the same batch as the scaffolds used for the following experiment in order to be able to obtain a correct flow measurement since the characteristics of the scaffolds can differ from batch to batch.

In another advantageous embodiment, the flow rate can be calibrated using an indicator dye, a light source, and a camera/video camera. By measuring the time it takes to fill out the outlet channels with the indicator, it is possible to calculate the fluid output from the central cavity. It is advantageous if at least the upper part of the device is transparent and the outlet channels being visible. It is further advantageous to this method if the lower part of the device has optical properties that make it easier to track the motion of the indicator. It is preferable, but not necessary, that the outlet channels have a simple geometry to ease calculations.

In a still further advantageous embodiment, the first and/or said second walls are/is partly interrupted.

The interruption of the walls of the recessed portions and/or the external means results in an additional opening of the recessed portion and/or the external means other than the first outlet orifice or the second outlet opening. Preferably, this additional opening is as big as to allow a scaffold or similar to be inserted into the recessed portions and/or external means.

Beneficially, the additional opening is arranged on the same side as the inlet orifice of the body. When the device is placed either in the liquid medium or just on a plain surface it is arranged with the inlet orifice directed away from the surface. Loading the device with for example scaffolds can then be performed from the top as well as from the side through the first outlet orifice as well as through the second outlet opening. This enables the device to be loaded more quickly as well as the correct placing of the scaffold in the recessed portions and/or the external means is easier. When loading the scaffolds through the first outlet orifice or through the second outlet opening may only be possible if the device is handled and turned for each scaffold to be placed. The turning to enable the first outlet orifice and/or the second outlet opening to be directed in a more upward position involves extensive handling of the device. This increases the risk of contamination as well as a risk of the scaffolds already placed in the device will move from a correct placement.

Furthermore, the additional opening of the recessed portions when open from the outlet channel to the first outlet orifice allows the external means to be loaded into the body from the top instead of from the side which is advantageous when working with small culture vessels. In addition, the additional opening may not stretch from the first outlet orifice to the outlet channel but only part of the way starting from the first outlet orifice in which case the external means can be loaded from the top of the body for part of it and then pushed into the recessed portion for the rest of the external means. This can be beneficial in order to obtain a correct and quick insertion of the external means into the recessed portions.

In a still further advantageous embodiment, the device for biological purposes such as cell culturing, enzymatic reactions or filtering of fluid further comprises means for delivery of drugs such as means for connecting a dispensing system to at least one small opening, preferably in said second plate; said at least one small opening is in connection with said aperture. In a still further advantageous embodiment, the means for delivery of drugs comprises a drug solution embedded in a leaching material; preferably said leaching material is attached on the second plate in connection with said aperture.

The term drug is here to be interpreted as any type of compound, which is normally added in terms of the uses of the device. This can be either drugs, growth factors like cytokines, hormones, or drugs in nanoparticle-based drug delivery systems. The compounds can be added either as a single compound or as a mixture of more compounds. The compounds can be added through one or more inlets into the aperture of the device. These inlets can be arranged at one or more of the following places: the first plate, the second plate, the sides of the aperture. The inlets can be connected to a dispensing system comprising a tube, a container comprising the compound of interests or eventually a mixture of compounds and means for moving the compounds from the container through the tube to the aperture of the device for the compound(s) to be mixed with the liquid medium. The means for moving the compounds can e.g. be a pump.

The compounds can be added to the aperture of the device in either continues manner or in a pulsed manner. A pulsed delivery of compounds can be obtained e.g. by adding a microprocessor based or mechanical timer function to the dispensing system As an alternative, the compounds can be embedded in a leaching material arranged in one or more places e.g. the first plate, the second plate or the sides adjoining the aperture of the device leaching the material into the liquid medium of the aperture. As an alternative an insert comprising an opening for liquid inflow can be placed into the inlet orifice of the body with a leaching material comprising one or more compounds adjoining the aperture. As a further alternative the compound and the leaching material can be a part of e.g. the first or second plate itself.

The release of the compounds from the leaching material can either be slow or quick depending on the type of leaching material used. Examples of leaching materials are e.g. polydimethylsiloxane (PDMS), erodible polymers (e.g. PLGA), layered silicates i.e. clays, gels and hydrogels.

Adding compounds directly into the aperture through an inlet or via a leaching material are beneficial since the amount of compound needed in order to obtain a given concentration is smaller, when added to the aperture than added to the liquid medium due to difference in volume.

In a further advantageous embodiment, the recessed portions and/or said external means are transparent.

The material of at least a part of the recessed portions or the external means can be made from colorless, transparent materials preferably, with low cell adhesion. When only a part of the recessed portions or the external means is made from the colorless, transparent material, this part is in which the scaffold is placed is clear of the body. This aids the researcher to visually inspect the scaffolds and e.g. the progression of cellular colonization of the cultured scaffold without overtly disturbing or terminating the setup.

In a further advantageous embodiment, the first and/or second wall at least partly comprises a porous material. In a still further advantageous embodiment, the inlet opening of said external means comprises a second regulatory mechanism to regulate the size of the outlet opening.

At least a part of the first or second wall e.g. the wall of the recessed portions and the wall of the external means, respectively, are made from an interconnected porous material, which can beneficially be inert and non-adhesive as well such as fiber or nanofiber mesh, sintered metal, glass, polymer beads, or porous membranes of e.g. ePTFE, polysulfone, celluloid. This will create peri-scaffold space that allows outflow of media through the scaffold and through the first and/or second walls. For example only the walls of the external means are made of an interconnected porous material while the walls of the recessed portions are not. In this case the flow of the liquid medium will end at the rim of the body. This will aid a better nutrient distribution in the cultured scaffolds.

In a further advantageous embodiment, the peri-scaffold space does not interface directly with the culture medium and is accessible through one or more ports on the device body. This is beneficial for culturing scaffolds with epithelial cells such as liver cells, secretory mammary cells, or kidney tubule cells; having distinct exocytotic and endocytotic functions for their apical and basal parts. It is the idea that the media in the pericellular space will have a different composition than that of the perfusing media because of the closer relationship to the cultured cells' basal parts. The ports in the body enable the sampling or regulation of the media in the peri-scaffold space.

The first outlet orifice of the recessed portions and/or the second outlet opening of the external means can either be open, partly open, or closed e.g. regulated by the first regulatory mechanism. Hereby, the amount outflow of the liquid medium through the scaffolds and the walls can be controlled. When the first outlet orifice or the second outlet opening is completely close the entire liquid medium is to flow through the scaffolds and the walls. The more the first outlet orifice and/or the second outlet opening is opened the more liquid medium is to flow out the first outlet orifice and/or the second outlet opening and the less is to flow through the scaffold and the walls.

Additionally, the inlet opening of the external means can be regulated to be either open, partly open or closed by a second regulatory mechanism with similar characteristics as the first regulatory mechanism. As an alternative the inlet opening can be partly or completely closed in a non-regulatory way either in the design of the external means or by inserting small inserts into the inlet opening and hereby closing it e.g. a plug. The liquid medium flow can hereby be directed into the second wall of the external means and following into the scaffold thereby creating an inflow of media into the scaffolds. Such a configuration can provide a better nutrient and cellular distribution within the scaffold.

In a further advantageous embodiment, the device for biological purposes such as cell culturing, enzymatic reactions or filtering of fluid comprises means for automated robotic manipulation such as markings in or on the device for fixation, localisation and identification to enable the robotic manipulation. These robotic manipulations include actions such as mechanical engagement with pneumatic or electric grippers for the purpose of moving the device from station to station, automated inspection of the cell culture, automated media change, automated scaffold seeding and scaffold unloading.

Furthermore, a method is described where a device for biological purposes such as cell culturing, enzymatic reactions or filtering of fluid is placed in liquid medium; said device comprises
- a body having a first and a second surface defining a body thickness there between, said surfaces are essentially parallel, and where said body is delimited by a rim;
- a aperture in the centre of the body; said aperture is covered at the first and second surface by a first and second plate, where the first and/or second plate comprises an inlet orifice allowing liquid medium into the aperture;
- means for rotating; said means for rotating is arranged in the aperture between the first and second plate;
- said rim comprises at least one recessed portion; said recessed portion is a cavity in the rim of the body comprising a first outlet orifice allowing the liquid medium to flow out of the body; and a first wall delimiting said recessed portion along said cavity;
- at least one outlet channel connecting the circular aperture with the recessed portion;
- optionally, an external means engages with the recessed portions, said external means comprises an inlet opening and a second outlet opening and a fluid connection between said inlet opening and said second outlet opening; said external means is a three-dimensionally shaped element delimited by a second wall defining an exterior surface of said external means;
- scaffolds in the recessed portion or the external means;
- where the liquid medium is pumped into the circular aperture of the body through the inlet orifice due to the rotation of the means of rotating and pumped through the at least one outlet channel, through scaffolds in the recessed portion or in the external means and out the first and/or second outlet orifice.

Additionally, a method where cells are seeded in or at the scaffolds before or after the scaffolds are arranged in the recessed portion or the external means is provided.

The device as described in this invention functions by simple means. Different types of scaffolds including cells or cells without the support of a scaffold are arranged into the recessed portions or the external means. Hereafter, the device is lowered into liquid medium in for example a beaker. The device is to be lowered carefully in order to avoid bubbles in connection with the inlet orifice and aperture. Bubble formation would obstruct a continuous flow of liquid medium by blocking either the inflow of liquid medium through the inlet orifice or the flow from the aperture and into one or more of the outlet channels.

The means for rotating is then activated, and creates a low pressure centrally inside the aperture of the body. The liquid medium is pumped into the aperture, through the outlet channels and past the cells. Hereby, the cells are continuously provided with fresh liquid medium and sufficient supply of nutrients and oxygen for even three-dimensional cultures.

When using a magnetic stirrer for driving the magnetic stirrer bar or impeller, it is important to have the device centred on the magnetic stirrer base plate. Otherwise the magnetic stirrer bar or impeller may not rotate consistently and the flow may be compromised. Therefore, in a further advantageous embodiment, the device will comprise integral or external means for reversibly securing a desired position of the central aperture within the liquid medium containing vessel. The means can e.g. be in the form of lateral spacers or fenders that are mounted on peripherally on the body. With the aid of these means, the vessel can then be securely positioned onto the magnetic stirrer base.

The simple use and set-up of the described device enables the device to be used in small incubators as well. Thus, this incubator can easily be used in hypoxic incubators.

Here, the cells can be cultivated in conditions more similar to physiological conditions where oxygen tension is lower than that of ambient conditions.

As another example, the device can easily be arranged in hermetically sealed containers due to the small size and because the rotation of the impeller/magnetic stirrer bar is caused by a non-mechanical force transmission. Hereby, lab-scale catalysed processes under e.g. supercritical $CO_2$-levels as well as cell culture studies with different levels of pressure are possible.

In addition, the device can be situated in a hermetically sealed container in order to avoid contamination during transport.

Furthermore, a method is described where proteins are immobilised on the scaffold; said proteins are able to interact with components of the liquid medium passing through the scaffold. In this method, the proteins can be enzymes, said enzymes interact with a substrate molecule, said substrate molecule is a component of the liquid medium passing through the scaffold comprising the enzymes. Additionally, in this method the proteins can be antibodies, antigens or ligands, said antibodies, antigens, or ligands interact with cells that are components of the liquid medium passing through the scaffold comprising the antibodies.

The liquid medium passes through the recessed portions and/or the external means and through the scaffold due to the means for rotating. Any components of the liquid medium, thus is passed through the scaffolds as well and are thus to be in contact with the immobilised proteins on the scaffold and affected hereby.

Additionally, in a cell-less application, chelating agents are immobilized on the scaffold; said chelating agent are able to interact with ions or larger molecules dissolved in liquid medium passing through the scaffold.

Immobilising enzymes on the scaffold brings the enzyme in contact with the flow of liquid medium and thus, the components of the liquid medium. Molecules, which are catalyzed by the enzymes immobilised on the scaffold, can be altered e.g. cleaved by the enzyme. The circulation of the liquid medium increases the percentage of substrate molecules metabolized.

Immobilising components for promoting cellular attachment is advantageous for purifying cells from the liquid medium. The immobilized components can be ligands for cell surface proteins—cell-specific or not—or other cell attaching proteins like cadherins, RGD- or IKVAV containing proteins such as fibronectin, vitronectin, laminin, collagen, osteopontin.

Furthermore, a method where the body is rotated by the means for rotating is described.

Rotating the means for rotating creates a low pressure inside the aperture and creates a continuous flow of liquid medium. However, the rotation can be increased to include the entire device. Hereby, the cells are exposed to a centrifugal force as well. The effect to the cells can be beneficial for proliferation and differentiation of certain cell types.

Furthermore, a method where the means for rotating comprises a magnet, said magnet is arranged in the circular aperture and where the magnet is rotated by the means of a external rotational magnetic field e.g. formed by a magnetic stirrer is described.

As a preferred form of the means for rotating, one may use a magnet. The magnet is inserted into the aperture of the body, which can preferably be circular. In connection with the body, a magnetic stirrer is arranged to enable the magnet in the device to rotate. Most magnetic stirrers are able to control the speed of the magnet. The rotation of the magnet is preferably above 120 rotations/min. in order to perform a stable, continuous flow. The flow is preferably between 0-0.8 ml/min, more preferred between 0.2-0.8 ml/min.

Furthermore, the magnet may be controlled in a time dependent manner. For example it can be controlled to rotate for two hours, then to stop rotating for another two hours, where after it rotates again for another hour. Thus, stop-motion flows past the cells can be obtained. Also flows with a more complex flow versus time behaviour may be setup, e.g. linear flow increase/decrease.

Furthermore, a method is described where a flow rate of the medium pumped through said inlet orifice is measured by the steps of attaching an external, non-leaky, compartment comprising an indicator solution comprising an indicator with a first concentration, C1, to the connective means at the inlet orifice;

allowing said indicator solution to be pumped into said aperture and pumped through at least one outlet channel;

measuring a second concentration, C2, of said indicator in said liquid medium with a given volume, V, after a given time, dt;

calculating said flow rate, Q, by a formula; said formula is given by $Q=-(C2*V)/((C2-C1)*dt)$.

A method for calibration of flow rate through the scaffolds is based on the indicator dilution technique known from e.g. clinical cardiac output measurements. For this instance, an external, non-leaky, compartment containing indicator solution of a given concentration, $C_1$, communicates with inlet through a channel with negligible hydrodynamic resistance. Rotation of the impeller will cause an overall time-independent flow, $Q_1$, of the indicator solution through the inlet and downstream through the scaffold and finally into the media immersing the Superfreac. At intervals, the immersing media, which has a determined starting volume, $V_2$, is sampled and the concentration of indicator is determined. The inlet flow rate is then calculated by $$Q=-(C_{2,dt}V2)/((C_{2,dt}-C1)dt)$$

Where dt is the time from flow start to sampling the indicator concentration, $C_{2,dt}$. It is important that compartment containing the indicator solution does not contribute with any confounding pressure on the indicator solution—neither due to gravity nor hydrostatic pressure differences across the compartment's walls. For these reasons it is preferable that the container walls are highly flexible and flaccid throughout the calibration procedure.

Furthermore, a method is described where the medium is pumped through the walls of said recessed portions and/or said external means.

Scaffolds are three-dimensional structures. The flow of liquid medium from the outlet channel to the first outlet orifice or the second outlet opening results in a flow through the scaffold in a one-directional manner. The distribution of liquid medium throughout the scaffold is hence not uniform. In the example, where cells are to be cultured inside the scaffold a uniform flow of liquid medium is essential to provide each of the cells with similar and optimal amounts of oxygen and nutrients. Forcing the flow of liquid medium to other directions such as more or less perpendicular to the direct flow from the outlet channel to the first outlet orifice and/or the second outlet opening enables the liquid medium to reach the outmost corner of the scaffold.

In order to obtain the alternative flow of liquid medium as described above interconnected porous walls of the recessed portions together with a closed or partly closed first outlet orifice would direct the flow of liquid medium from the outlet channel and out through the pores of the walls of the recessed portions. Similarly, interconnected porous walls of the external means together with closed or partly closed second outlet openings will direct the flow of liquid medium from the outlet channel and at least partly out through the walls of the external means. The flow of liquid medium will continue through these walls as well if the walls of the recessed portions are also formed from an interconnected porous material. However, if the walls of the recessed portions are not made of a porous material the liquid medium will flow along the external means and out the first outlet orifice, while part of the liquid medium will enter through the interconnected porous walls of the external means, through the scaffold and out the second outlet opening if this is partly opened.

The flow of the liquid medium can be changed to an inflow instead of an outflow through the scaffold as described above. This can be created by inserting an external means comprising interconnected porous walls into a recessed portion, where the inlet opening of the external means is closed or partly closed. The liquid flow is hereby forced into the space between the external means and the recessed portions. Due to the interconnected porous walls of the external means the liquid medium then penetrates into the external means and through the scaffold before it flows out through the second outlet opening.

The invention is also directed to the use of a device for biological purposes such as cell culturing, enzymatic reactions or filtering of fluid as previously described where the device is used for obtaining perfusion flow. Furthermore, the invention is directed to the use of a device for culturing of cells or purification of cells from liquids. Furthermore, the use of a device as previously described where the device is used for the culturing of 3D cultures.

This device can be used in order to obtain reproducible cell culture studies. The flow circulates the liquid medium inside the beaker and hence, diffusion rates of nutrients and oxygen is increased to promote the proliferation and differentiation of cells in 3D cultures. In addition, the circulation of the liquid medium makes the use of pumps unnecessary, in that the means for rotating is the pump in this system.

Furthermore, the device for biological purposes such as cell culturing, enzymatic reactions or filtering of fluid can be used for the purification of cells from liquids given that the right scaffold is situated in the recessed portions. The liquid containing the cells is either added through the inlet orifice directly, or the liquid containing the cells is the liquid medium into which the device is put down. The cells attaches to the surface of the scaffold when the liquid medium passes through the outlet channels and through the scaffold either inserted in the recessed portions or the external means. The cells attaching to the scaffold can either be specific types of cells or all cells capable of attaching. Specific types of cells can be attached by e.g. linking specific types of antibodies to the surface of the scaffold. As an example, Stro-1 or CD44 antibodies can be linked to the scaffold and used for attaching to MSCs from the bone marrow.

The liquid to be purified can for example be blood from where e.g. stem cells can be purified. In this case, the scaffold is to be a biocompatible polymer with a pore size of 100-200 μm comprising interconnected porosity.

Overall, it is of course essential that the surfaces of the device to be in contact with the liquid containing cells do not comprise material with properties able to efficiently bind to cells, because else the cells would stick to the exposed surface in contrast to the scaffold. Thus, the exposed surface can for example be treated with hydrophobic polyfluoro ethylene propylene or silicone A sustained flow of liquid medium past the cells results in that the cells can be grown in 3D cultures. Hereby, cells for tissue engineering like tissues for liver, bone and cartilage repair and/or replacement can be grown.

As an example the repair of bone can be performed in the following way: A suitable scaffold is seeded with stem cells or bone progenitor cells. The scaffold is placed inside the external means and this is placed in the recessed portion or the scaffold is arranged directly in the recessed portions. A magnet is arranged inside the aperture of the body and the device is then lowered into a beaker containing liquid medium. The beaker is situated on top of a magnetic stirrer inside a $CO_2$-incubator and the magnetic stirrer is activated. A flow of liquid medium is passed through the scaffolds and with time the cells proliferate and differentiate into mineralising cultures. After due time, the scaffold is removed from the device and can be transferred to the skeleton/bone structure of a patient.

Furthermore, the invention is directed to the use of a device for biological purposes such as cell culturing, enzymatic reactions or filtering of fluid for bulk-treatment of scaffolds.

Depending on the material of the device, the liquid media used for the bulk-treatment of scaffolds or other components with porous characteristics can be acids, bases, organic solvents, salt solutions or the like. Any component resident inside the scaffold e.g. remains from the formation of the scaffold is flushed out during the bulk-treatment.

Furthermore, the invention is directed to the use of a device for enzymatic reactions, where immobilised enzymes act on proteins provided by the liquid medium.

Cells or enzymes can be immobilised on scaffolds in order to act on the liquid passed through the scaffolds. They can either be immobilised by covalent attachment, adsorption, entrapment in polymeric gels, cross-linking with bi-functional reagents or encapsulations as described in Klibanov A M, "Immobilized enzymes and cells as practical catalysts", Science 219:722-7, (1983). The immobilisation of enzymes or cells enhances the efficiency of the process e.g. the cleavage of a protein.

Throughout the application the term liquid medium is used in order to describe the liquid performing the flow through the device. The liquid medium can be any type of liquid appropriate for the given situation. As an example, the liquid medium used when culturing cells is preferably a cell culture medium, normally considered for the specific types of cells.

Furthermore, the invention is directed to the use of a device, where shed blood for postoperative autologous transfusion is filtered by flowing through scaffolds.

Hereby, the shed blood is led through the scaffolds in order to purify the blood. Preferably, scaffolds with a pore size of around 40, 80, and/or 200 μm is to be used.

DETAILED DESCRIPTION OF THE INVENTION

Figure 1:
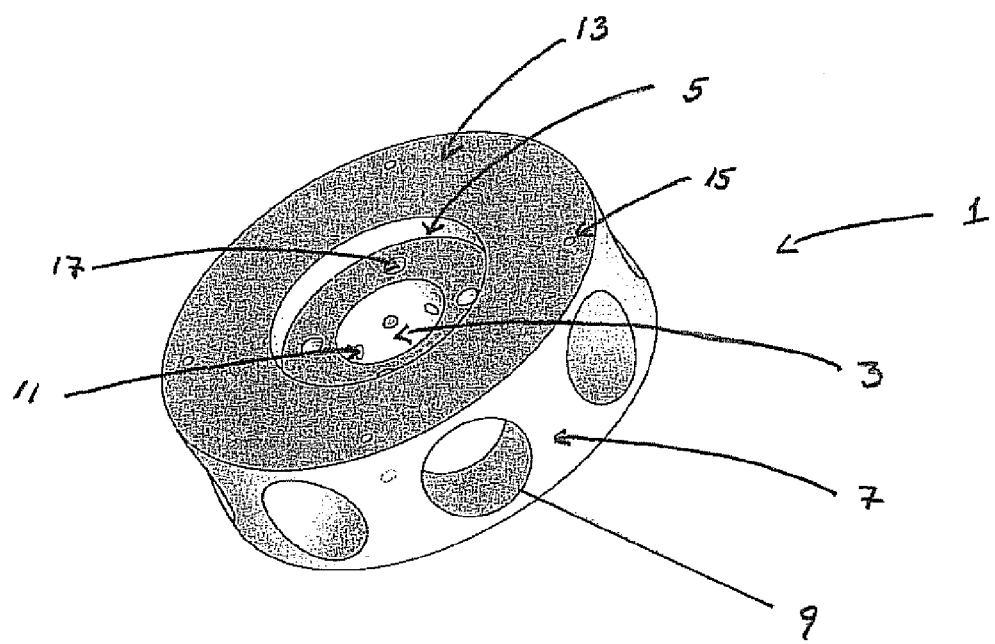
FIG. 1 illustrates a top-side view of the body.

FIG. 1 illustrates a top-side view of the body 1 of the device. In this particular embodiment, the aperture 3 in the body 1 is arranged in a lowered circular orifice 5. At the rim 7 of the body 1 eight recessed portions are present out of which five 9 are observed at the drawing. In addition, outlet channels 11 are observed in the aperture 3 of the body 1. At the surface 13 of the body 1, four orifices 15 are provided. These orifices 15 are capable of engaging with pins which can combine multiple devices on top of one another.

Figure 2:
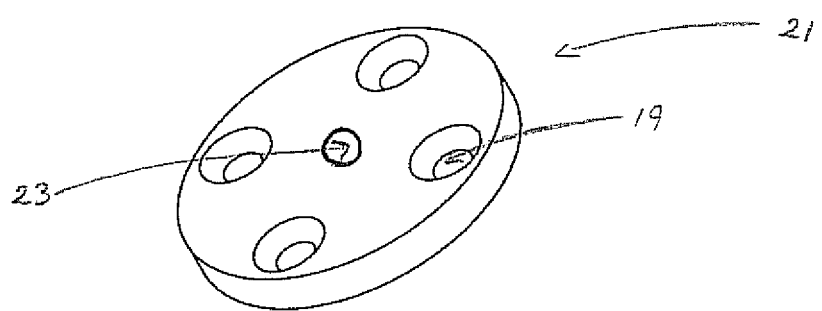
FIG. 2 illustrates a first plate with an inlet orifice.

Inside the lowered orifice 5, four openings 17 are seen. These four openings 17 secure the engagement with the openings 19 of the first plate 21. An example of a first plate 21 is observed in FIG. 2 where a top-side view is illustrated. The first plate 21 can be attached to the body 1 by means of for example screws through the openings 19 of the first plate 21 and the openings 17 of the body 1. FIG. 2 further illustrates an inlet orifice 23 through where liquid medium can enter into the aperture 3 of the body 1.

Figure 3:
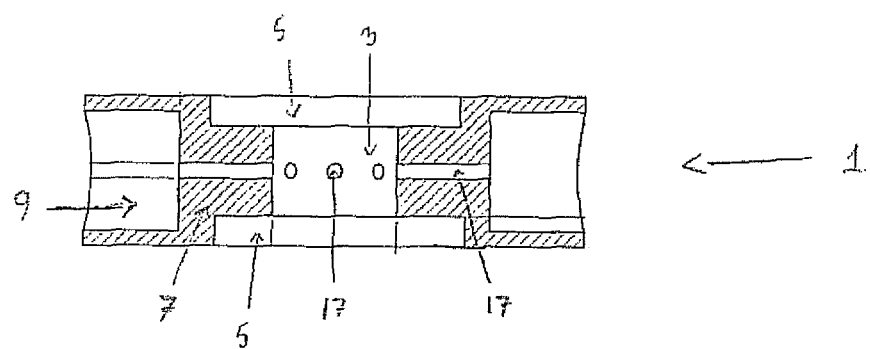
FIG. 3 illustrates a side view of the body.

FIG. 3 illustrates a side view of the body 1. The recessed portions 9 are observed at the rim 7 of the body 1. Furthermore, the aperture 3 is illustrated along with outlet channels 17 combining the aperture 3 and the recessed portions 9. Furthermore, lowered orifices 5 are observed on both sides of the body 1. First and second plates 21 can be inserted into these lowered orifices 5. As an alternative, the first and second plates 21 can be an integrated part of the body 1. The second plate is preferably similar to the first plate except for the inlet orifice, which is preferably only present on the first plate 21.

Figure 4:
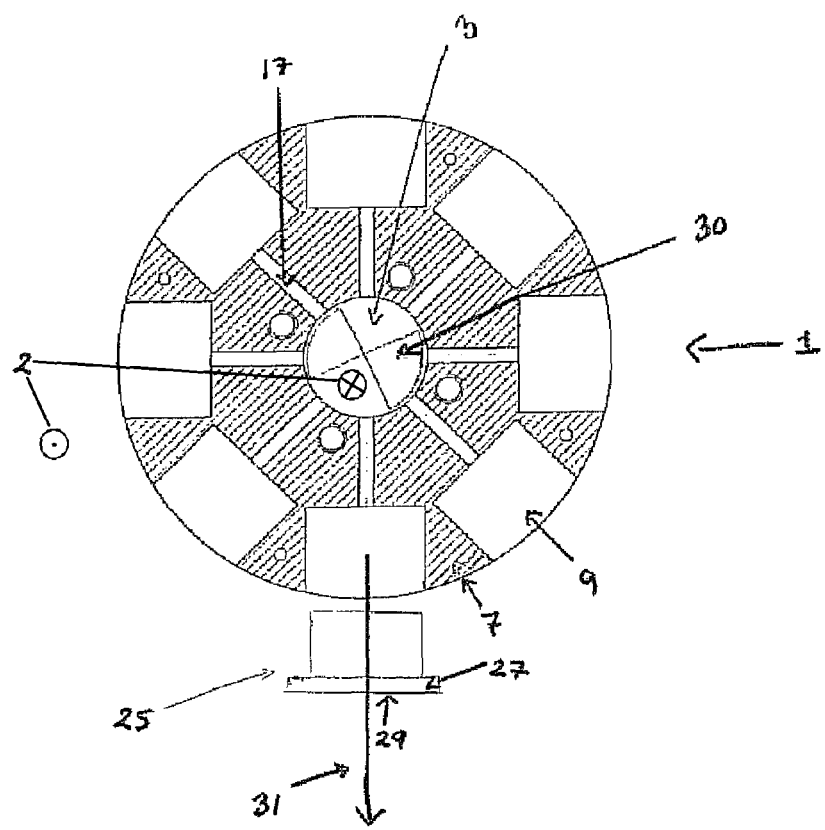
FIG. 4 illustrates a top view of the body.

FIG. 4 illustrates a top view of the body 1. The aperture 3 is observed in the centre of the circular body 1. Furthermore, eight recessed portions 9 are illustrated at the rim 7 of the body 1. The outlet channels 17 are also illustrated. The outlet channels 17 are integrated in the body 1 of the device and are, hence, not in contact with the surroundings. The integration of the outlet channels 17 is essential in order to obtain a proper flow and to avoid contamination with e.g. bacteria and fungus.

Below the body 1 in FIG. 4, an external means 25 is illustrated as a first regulatory mechanism to regulate the size of the outlet opening. This particular embodiment is a press-fit version of external means 25 and furthermore, comprises a flange 27 along the outer rim 29 of the external means 25. A scaffold can be inserted in the external means 25 and arranged towards the rim 29 where the flange 27 is situated. Preferably, the second outlet orifice at the rim 29 is shaped in order minimize risk of bubble entrapment during scaffold loading into the recessed parts of the body while still supporting the placement of the scaffold and preventing it from moving in direction of the flow 31. This is especially important for high flow applications where the force exerted on the scaffolds gets significant.

The means for rotating is in FIG. 4 illustrated as a magnet 30 formed to fill the opening of the aperture and with two rotating blades, which during rotation leaves the openings between the outlet channels 17 and the aperture 3 free for movement of liquid medium or closed, whereby no liquid medium is able to move into the outlet channels 17. The magnet 30 is a second regulatory mechanism to regulate the size of the inlet opening, and creates an electrical field 2. Hereby, a time-varying flow is created during the rotation of the magnet 30.

Figure 5:
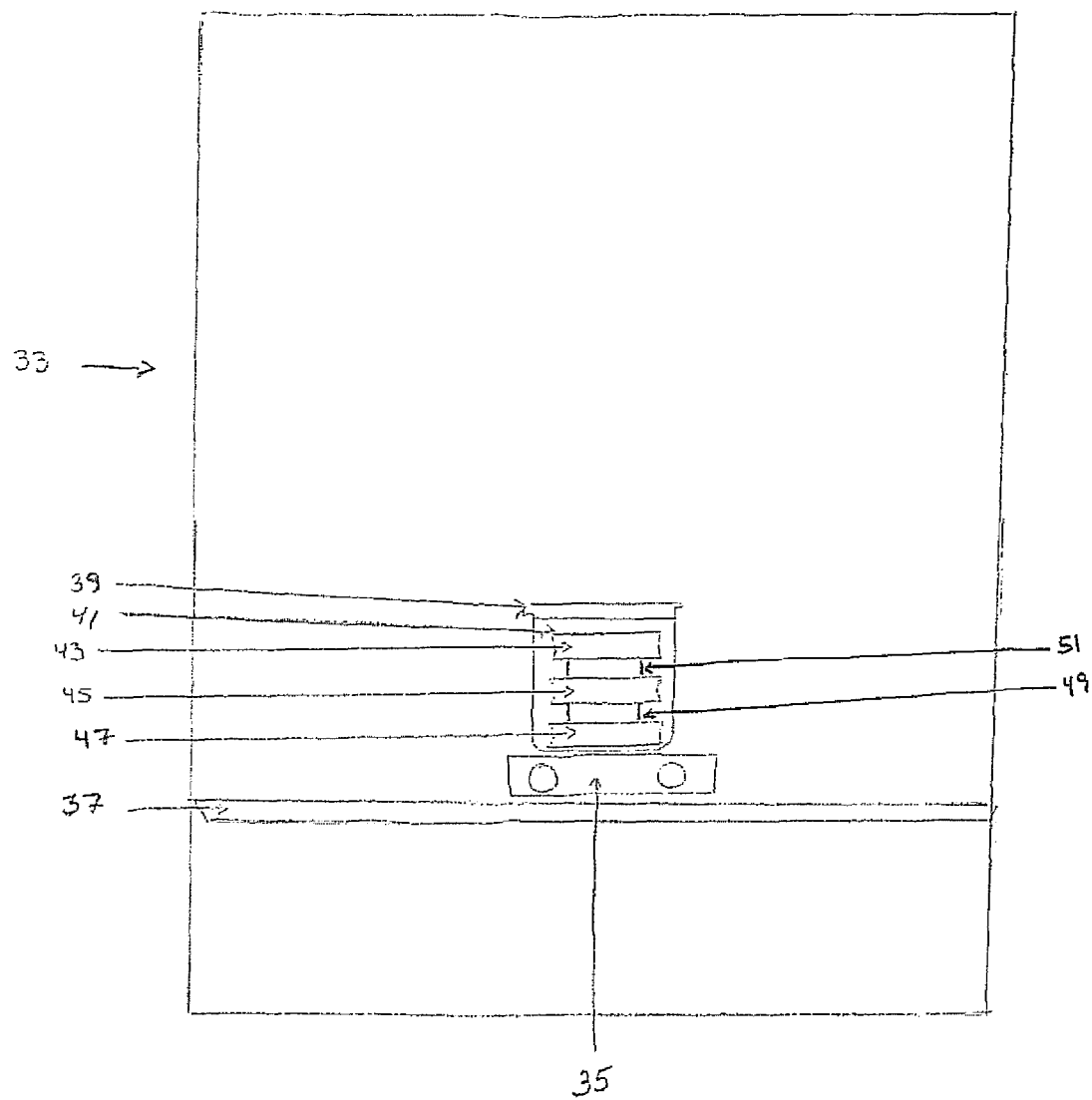
FIG. 5 illustrates the device inside an incubator.

FIG. 5 illustrates a set-up of the device inside a $CO_2$-incubator 33. Inside the $CO_2$ incubator 33, a magnetic stirrer 35 is arranged on a shelf 37. On top of the magnetic stirrer a beaker 39 is placed. Liquid medium 41 is present inside the beaker 39 along with the three devices 43, 45, 47. The first device 47 is arranged at the bottom of the beaker 39. The first device 47 is connected to the second device 45 via spacers 49 and the second device 45 is connected to the third device 43 via other spacers 51. In this manner, multiple devices can be stacked and rotated in a single beaker 39. Each of the devices 43, 45, 47 comprises a magnet in their aperture. This magnet is affected by the magnetic field created by the magnetic stirrer 35, and hence, a flow is created in each of the devices. Although the magnetic field strength rapidly decreases with the distance to the magnetic stirrer base, as long as the torque on the magnetic stirrer bars is sufficient to drive them all at the desired rotational speed (RPM), the flow through all the stacked devices will be the same. For the proper function of the system it is essential that the liquid medium covers all of the devices.

Figure 6:
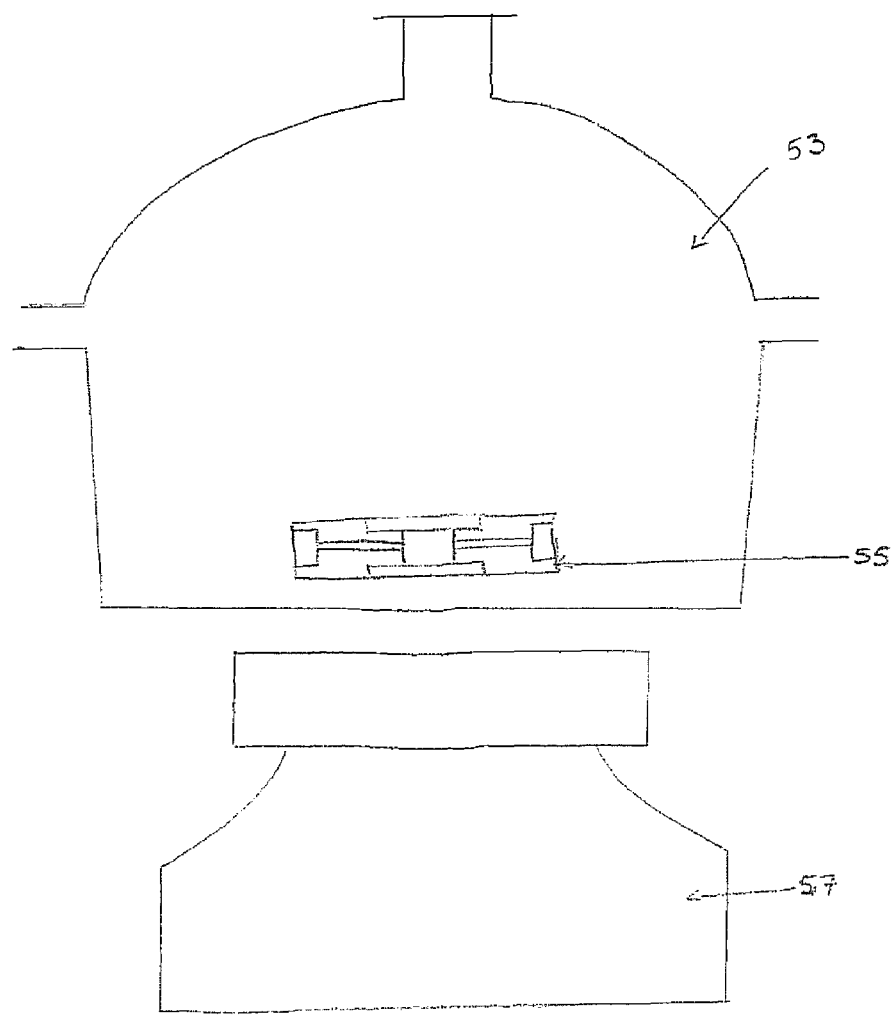
FIG. 6 illustrates the body of the device inside a pressure chamber.

FIG. 6 illustrates the device arranged inside a pressure chamber 53. The body 55 of the device is placed inside the pressure chamber 53. Outside the pressure chamber a magnetic stirrer 57 is situated whereby the means of rotating inside the central aperture of the device can be rotated and a flow of liquid medium through the outlet channels is created.

Figure 7:
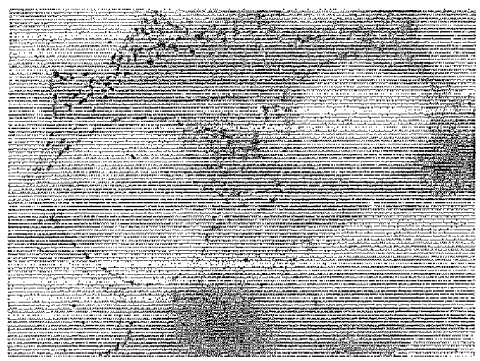
FIG. 7 illustrates hMSCs-tert cells cultured on scaffolds under static conditions (7A) and in the device of the invention (7B)
Figure 7:

FIG. 7A and FIG. 7B illustrates an example on cells cultured under static conditions (7A) and cells cultured using the device of the invention (FIG. 7B). Porous polycaprolactone (PCL) scaffolds with dimensions =10 mm, h=6 mm, and a porosity of 93% were fabricated by fused fibre deposition modeling (Syseng, Germany). The extruded fibres displayed a thickness of roughly 170 µm and were arranged with a pitch of 0.8 mm. In order to increase hydrophilicity, the scaffolds were treated with 1.25 M NaOH for 16 h and a subsequent EtOH gradient.

Eight scaffolds were inserted into the external means and situated in wells of 6 well plates with one scaffold situated per well. Four scaffolds (control) were situated directly in 6 well plates with one scaffold per well. hMSC-tert cells (Simonsen J L et al., "Telomerase expression extends the proliferative life-span and maintains the osteogenic potential of human bone marrow stromal cells", Nat. Biotechnol., 20(6):592-6, (2002)) were thereafter seeded at a concentration of $2 \times 10^6$ cells per scaffold.

The cells were left for 2 hrs in a $CO_2$-incubator for the cells to adhere. Hereafter, 7.5 mL of cell culture medium (10% fetal calf serum in DMEM) was added to the scaffolds.

The next day, the control scaffolds were moved to new 6 well plates, while the scaffolds arranged in the external means were situated in the device. The controls were added 15 mL of medium per well and medium was changed once a week. All 12 scaffolds were treated with cell culture medium containing 10% fetal calf serum in DMEM added 10 nM Vitamin D The cells were cultured for 2 weeks before the growth of the cells were investigated. The scaffolds were cut into thin sections and stained with hematoxylin and eosin stain, whereafter the morphology of the cells attaching to the scaffolds was investigated. The static cultivated cells show a fibroblast-like morphology with elongated cells, while the cells cultured on scaffold introduced into the external means of the device of the invention have larger nuclei and a more osteoblast-like morphology as illustrated in FIG. 7A and FIG. 7B, respectively. The scaffold is illustrated as white sections.

Figure 8:
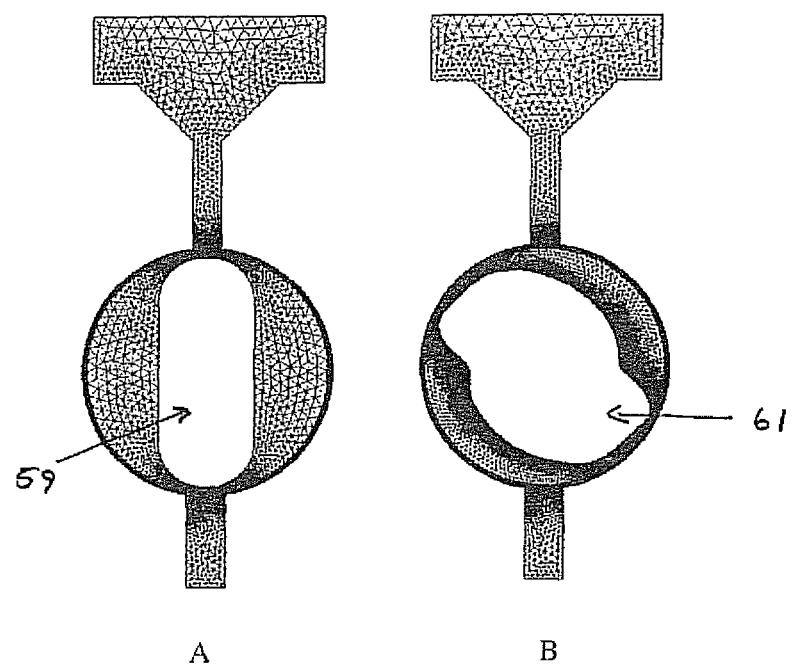
FIG. 8 illustrates a standard shape of a magnetic stirrer (8A) and a second shape of a magnetic stirrer (8B)

In FIG. 8 the shape of the rotating means is investigated and its influence on the pressure build up in front of the scaffold is investigated using computational fluid dynamics. Two cam designs are numerically generated. One resembles a standard magnetic stirrer (59) as illustrated in FIG. 8A. The second shape (61) is generated from a curve fitted to data describing the central aortic pressure wave as illustrated in FIG. 8B.

The 3D geometry of the flow chamber is approximated in Comsol, (COMSOL 3.5a, COMSOL Inc, Stockholm, Sweden) by a 2D geometry. The central aortic pressure wave as measured by Chen et al. in Circulation, 95:1827-1836, (1997) is for two periods approximated by a spline curve in Matlab® R2008b (The MathWorks Inc., Natick, Mass., USA). This curve is coordinate transformed from Cartesian to polar in order to generate as closed curve, thereby determine that one rotation of the impeller is equivalent to two periods of the aortic pressure wave. Its amplitude is scaled to fit into the flow chamber cavity and the complete geometry is assembled in Comsol and discretised as shown.

FIG. 8 illustrates the discretised 2D space in which the Navier-Stokes problem is solved for two different shapes of the rotating means.

Figure 9:
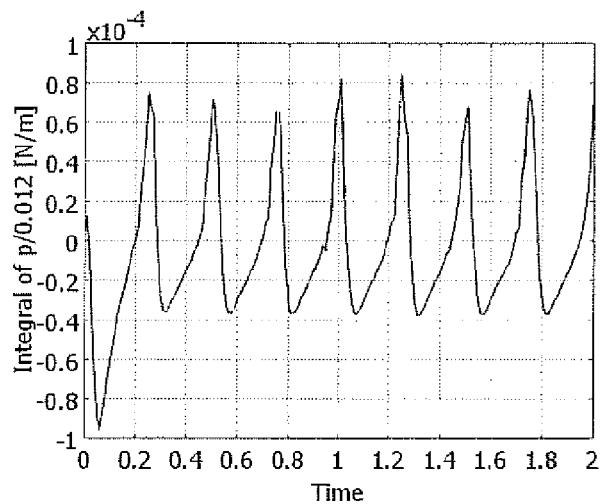
FIG. 9 illustrates the pressure variation for a standard magnetic stirrer (9A), the pressure variation for the second shape of a magnetic stirrer (9B), and the central aortic pressure wave (9C)
Figure 9:
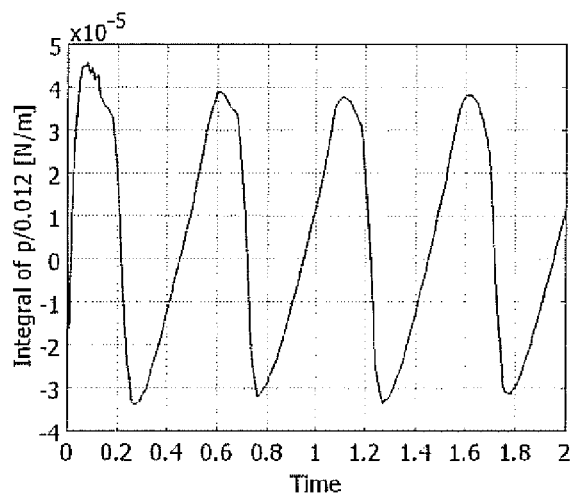
Figure 9:
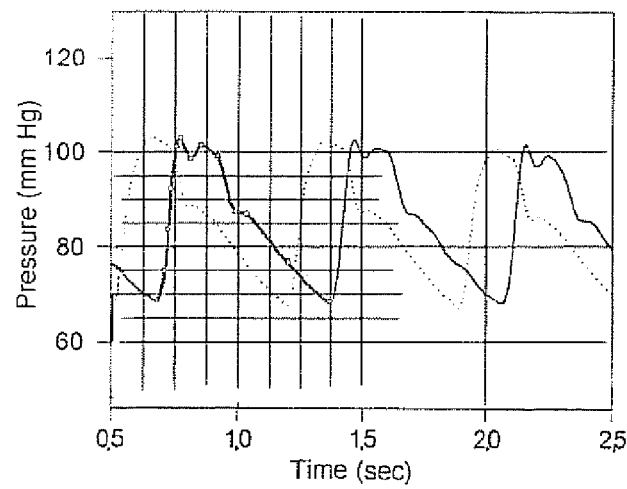

The incompressible Navier-Stokes partial differential equation is then numerically solved by the finite element method using Comsol in two connected coordinate systems, a static reference system, and a rotating system including the rotating means. The rotation of the impeller is set to 60 rpm and the properties of water are applied in the fluid domain. Boundaries are modeled as open over the inlet/outlet edges and a no-slip condition is implied at all other edges describing the interface between the structure and the fluid. The pressure variation over the upper edge, which is located just in front of the scaffold, is plotted for the two cases in FIG. 9 together with the measured central aortic pressure wave. FIG. 9A illustrates the pressure variation for a standard magnetic stirrer; FIG. 9B illustrates the pressure variation for the second shape of a magnetic stirrer, while FIG. 9C illustrates the central aortic pressure wave.

Hereby, it have been demonstrated that the relative pressure variations in front of the scaffold are shown to be controllable by the shape of the rotation means. Through shape optimization it is possible to induce a pressure field over the cells within the scaffolds that relatively mimics the pressure fluctuation generated over a heart cycle.

Figure 10:
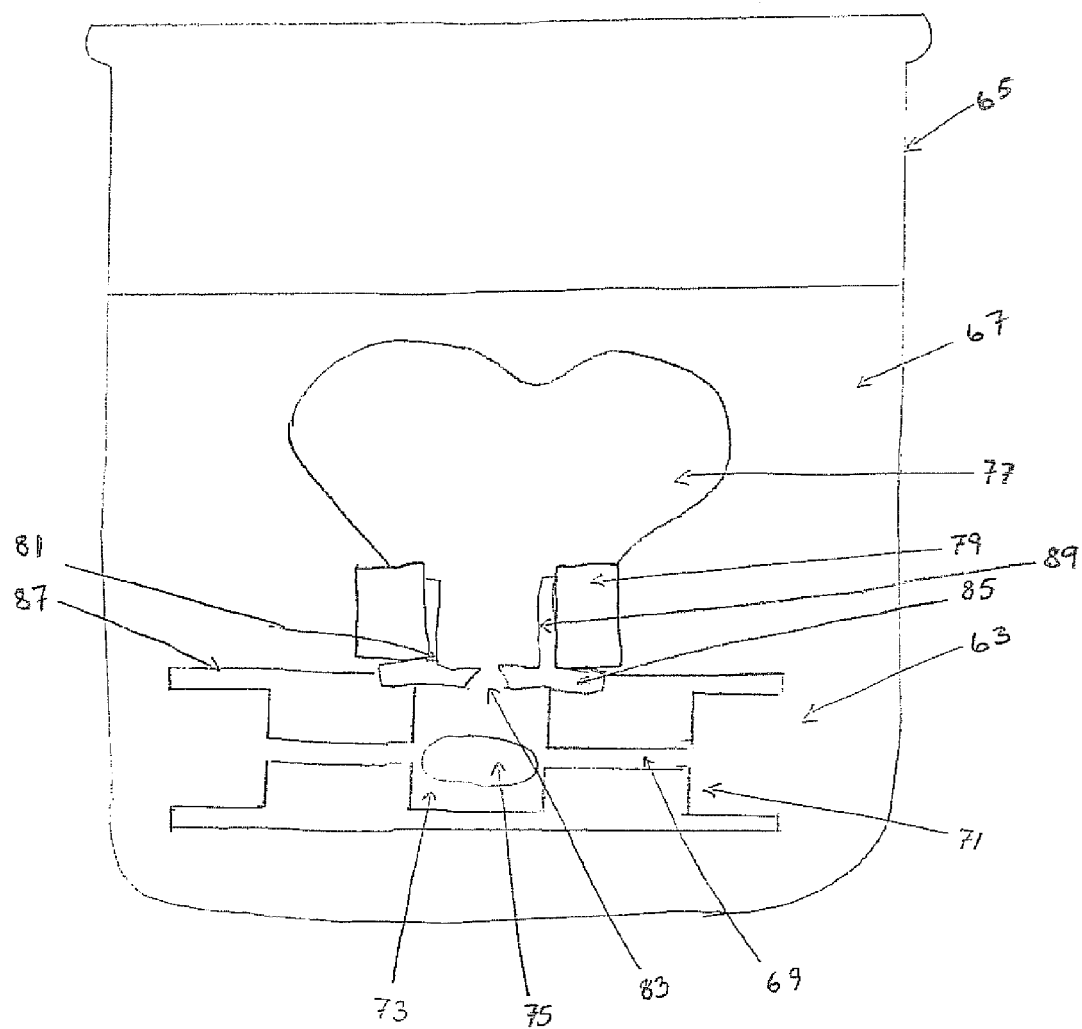
FIG. 10 illustrates an external, non-leaky compartment attached to the body.

FIG. 10 illustrates the setup for calibrating the flow rate of the device 63. The device 63 is arranged in a beaker 65 and immersed in liquid medium with a given volume 67. The device 63 is illustrated with a body comprising outlet channels 69, recessed portions 71, and an aperture 73 where a magnet 75 is arranged. An external compartment 77 is attached to connective means 79, 81 to the inlet orifice 83. In this particular embodiment, the connective means 79, 81 comprises two parts, preferably ring-shaped. The first part 81 comprises a flat ring 85 engaging with the first surface 87 of the body 71. The flat ring 85 further comprises a flange 89 perpendicular to the flat ring 85, where the flange 89 engages with the external compartment 77 by being inserted on the inside of the opening of the external compartment 77. On the outside of the external compartment 77 the second part 79 of the connective means is secured. The second part 79 is preferably a ring, which can be tightened after it has been secured to the connection. This ensures that the connection of the external compartment to the inlet orifice 83 prevents leakage, whereby the solution of the external compartment is prevented from flowing anywhere else than into the aperture 73.

In order for the flow calibration to be calculated the volume of the liquid medium 67, the concentration of the indicator in the solution contained in the external compartment 77 as well as the concentration of indicator in the liquid medium 67 after a given time. Activating the magnet 75 in the aperture 73 pumps solution from the external compartment 77 into the aperture 73, through the outlet channels 69, through the recessed portions 71, and into the liquid medium 67, where the solution is diluted. Beneficially, the setup for the calibration is similar to the setup in the experiment.

Figure 11:
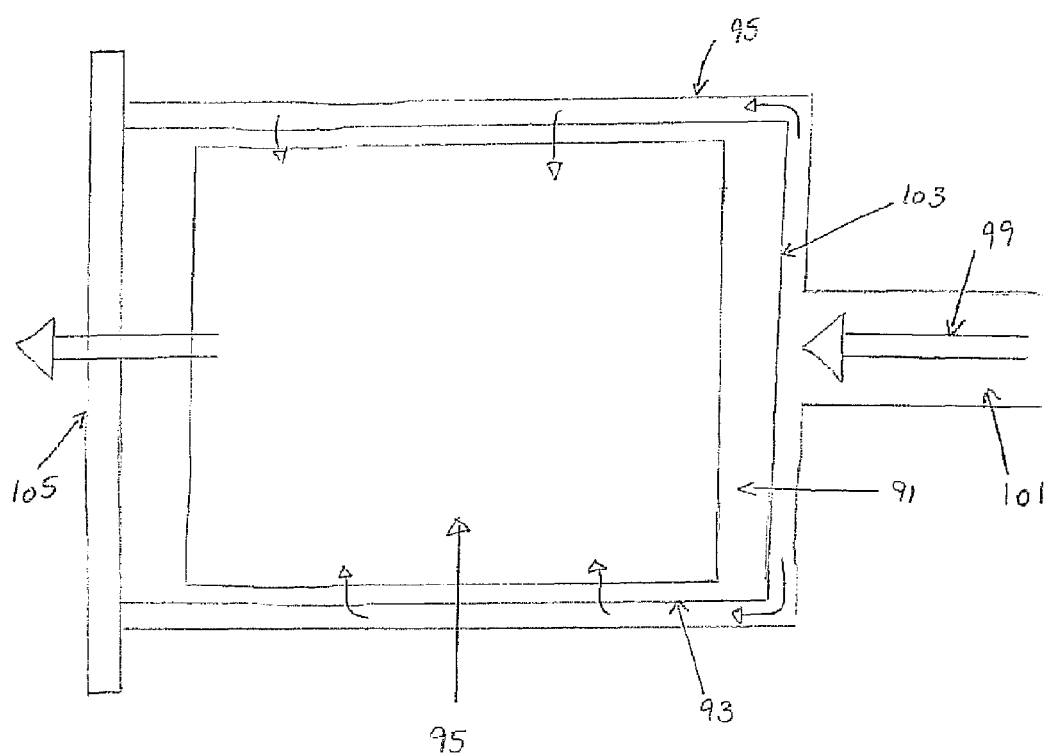
FIG. 11 illustrates the flow of liquid medium when the external walls comprise a porous material.

FIG. 11 illustrates an example of an inflow mechanism, where the liquid medium penetrates the external means 91 through the wall 93. The recessed portion 95 comprises an external means 91 into which a scaffold 97 is inserted. The liquid medium 99 (as illustrated by arrows) flows through the outlet channel 101 into the recessed portion 95 but not directly into the external means 91 since the inlet opening 103 is closed. Instead the liquid medium 99 flows along the external means 91 and into the external means 91 and the scaffold 95 through the interconnected porous walls 93 of the external means 91. The liquid medium 99 leaves the scaffold 95 and the external means 91 through the second outlet opening 105.

FIG. 12 illustrates a two-part form of the device comprising a bottom part viewed from the top (A) and the bottom (B); a top part viewed from the top (C) and the bottom (D); and an assembled device (E).

Figure 12A:
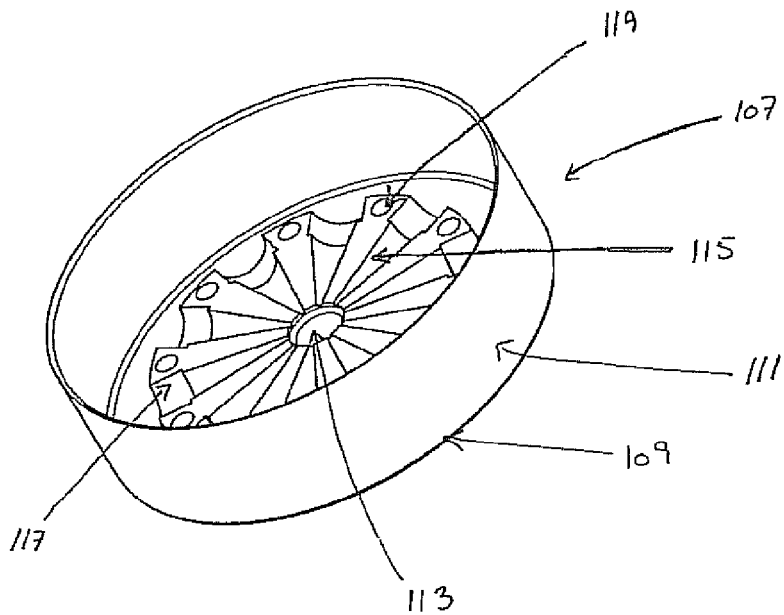
FIG. 12 illustrates a two-part form of the device comprising a bottom part viewed from the top (A) and the bottom (B); a top part viewed from the top (C) and the bottom (D); and an assembled device (E).
Figure 12B:
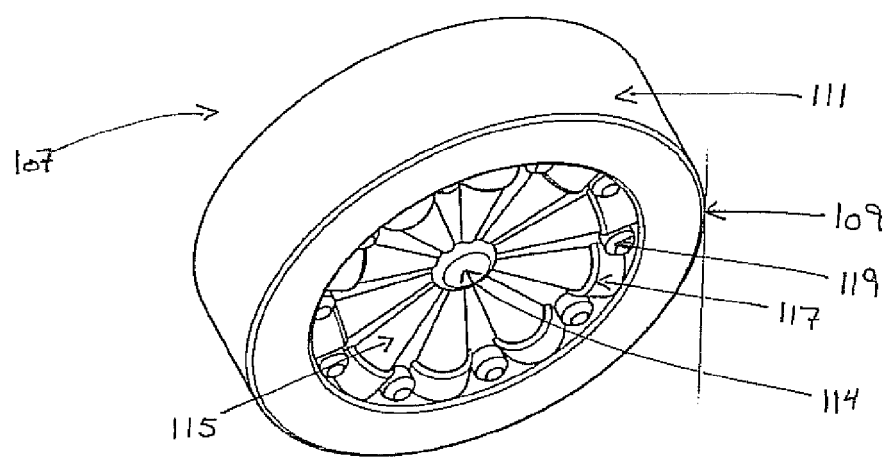

The bottom part 107 as illustrated in FIG. 12A in a top view and in FIG. 12B in a bottom view. The bottom part 107 is an integrated part of a vessel 109 comprising an outer rim 111 and a lid (illustrated in FIG. 12E). The bottom part 107 of the device comprises a bottom aperture 113 covered by a second plate 114 in fluid connection with lower parts of outlet channels 115 and recessed portions 117. The outlet channels 115 and recessed portions 117 are formed as cones divided longitudinally and with the smallest diameter of the cone closest to the bottom aperture 113. In the area between the recessed portions 117 openings 119 are present.

Figure 12C:
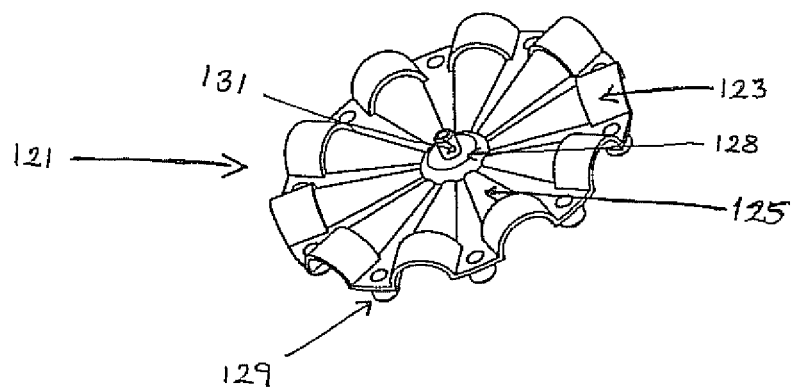
Figure 12D:
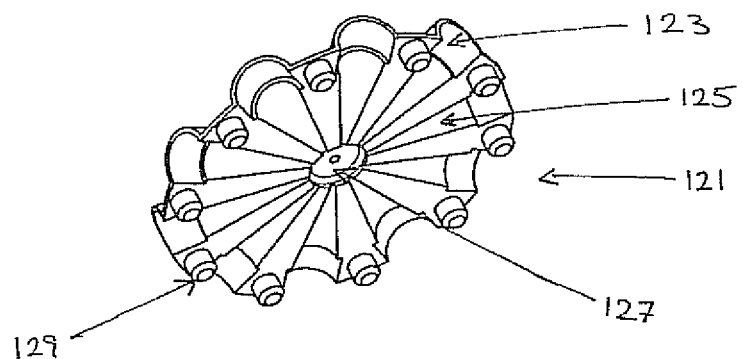

Complementarily, the top part 121 of the device is illustrated in a top view in FIG. 12C and in a bottom view in FIG. 12D. The top part 121 comprises upper parts of outlet channels 123 and recessed portions 125, which are in fluid connection with a top aperture 127. The outlet channels 123 and recessed portions 125 are formed as cones divided longitudinally and with the smallest diameter of the cone closest to the top aperture 127. In the area between the recessed portions 125 protrusions 129 are present. Furthermore, an inlet orifice 131 in fluid connection with the top aperture 127 covered by a first plate 128 is illustrated in FIG. 12C.

It is implicitly to be understood that the openings 119 can be present on the top part 121 while the protrusions 129 are present on the bottom part 107. Furthermore, it is to be understood, that though openings 119 and protrusions 129 are present in each space between the recessed portions 117, 125 they can be present in for example each second or third space as long as the top part 121 and bottom part 107 can be firmly connected in order not to separate during rotation. In this figure means for assembling the two part together is protrusions and openings, however, it is to be understood that the means for assembling can take other forms as well.

Figure 12E:
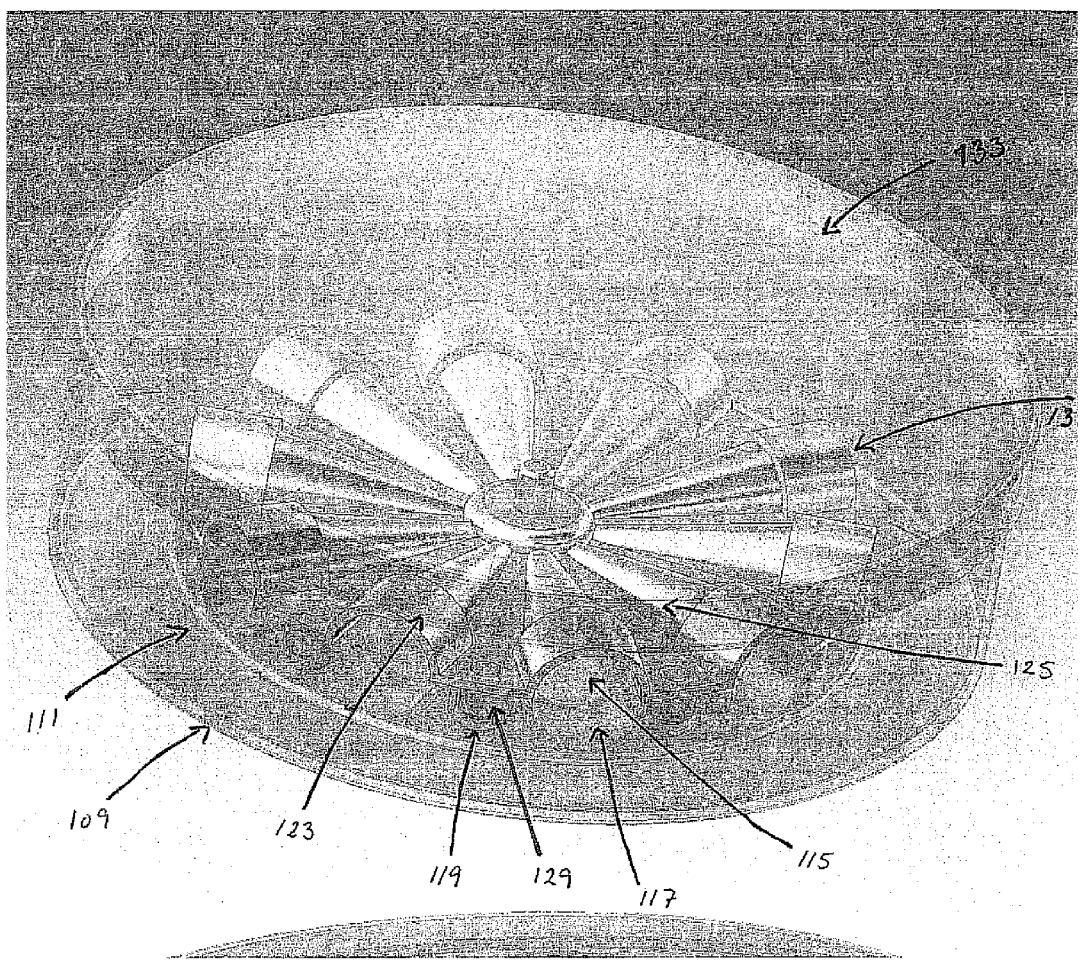

FIG. 12E illustrates an assembled device/body 135. Assembling of the bottom part 107 and the top part 121, thus results in an assembled device 135 with a first and second surface comprising an aperture superposed from the first aperture 127 and the second aperture 113, where the aperture is covered by a first plate 128 and a second plate 114. Liquid is pumped through an inlet orifice 131 present in the first plate 128 and into the aperture by means of rotating. The assembled device 135 further comprises at least one outlet channels formed by the superposing of an upper part 125 and a lower part 115 from the top part 121 and bottom part 107, respectively. In addition, the body 135 comprises at least one recessed portion formed by the superposing of an upper tunnel-shaped section forming the upper part of the recessed portion 123 and a lower tunnel-shaped section forming the lower part of the recessed portion 117, which corresponds in size and shape and herby forms a first outlet orifice. The so formed outlet channel fluidly connects the aperture with the recessed portion, and the liquid can leave the body through the first outlet orifice formed by the tunnel-formed sections.

During use, scaffolds are placed in the recessed portions 117 of the bottom part 107 and a magnet is arranged in the bottom aperture 113. The top part 121 of the device is then arranged with the protrusions 129 into the openings 119 e.g. by press-fit and an assembled device 135 is formed as illustrated in FIG. 12E. Liquid medium is poured into the vessel 109 and a lid 133 is placed on top of the vessel 109. The rim 111 of the vessel 109 is considerably higher than the device 135 i.e. the top part 121 and the bottom part 107 assembled in order for medium to be well above the assembled device 135.

The invention claimed is:

1. A device for biological purposes such as cell culturing, enzymatic reactions or filtering of fluid wherein the device comprises
    a body having a first and a second surface defining a body thickness there between, and where said body is delimited by a rim;
    an aperture in the center of the body; said aperture being covered at the first and second surface by a first and second plate, where the first and/or second plate comprises an inlet orifice allowing liquid medium into the aperture;
    means for rotating; said means for rotating being arranged in the aperture between the first and second plate;
    said rim comprises at least one recessed portion; said recessed portion is a cavity in the rim of the body comprising a first outlet orifice allowing the liquid medium to flow out of the body; and a first wall delimiting said recessed portion along said cavity;
    at least one outlet channel connecting the aperture with the recessed portion;
    wherein the device further comprises an external means, where the external means engages with the recessed portions of the body and comprises an inlet opening and a second outlet opening and a fluid connection between said inlet opening and said second outlet opening; and wherein
    said external means is a three-dimensionally shaped element delimited by a second wall defining an exterior surface of said external means.

2. The device for biological purposes such as cell culturing, enzymatic reactions or filtering of fluid according to claim 1, wherein said first and second surfaces are essentially parallel.

3. The device for biological purposes such as cell culturing, enzymatic reactions or filtering of fluid according to claim 1, wherein the device comprises means for centring and levelling the device in a liquid medium containing vessel.

4. The device for biological purposes such as cell culturing, enzymatic reactions or filtering of fluid according to claim 1, wherein the first plate and/or the second plate is/are an integrated part of the device.

5. The device for biological purposes such as cell culturing, enzymatic reactions or filtering of fluid according to claim 1, wherein said device is an integrated part of a vessel.

6. The device for biological purposes such as cell culturing, enzymatic reactions or filtering of fluid according to claim 1, wherein said device is divided into two parts, a top part and a bottom part, along a plane substantially parallel to said first or second plate, and where said plane further divides said at least one recessed portion and said at least one outlet channel.

7. The device for biological purposes such as cell culturing, enzymatic reactions or filtering of fluid according to claim 1, wherein the external means comprises an outer thread where said outer thread engages with an inner thread provided in an internal means when the external means is engaged with the recessed portions.

8. The device for biological purposes such as cell culturing, enzymatic reactions or filtering of fluid according to claim 1, wherein the outlet channel is conically shaped, where the smallest cross sectional area of the conically shaped outlet channel is in connection with the aperture.

9. The device for biological purposes such as cell culturing, enzymatic reactions or filtering of fluid according to claim 8, wherein the conical shape of the outlet channel continues in at least a part of the recessed portion; said part of the recessed portion being in contact with the outlet channel.

10. The device for biological purposes such as cell culturing, enzymatic reactions or filtering of fluid according to claim 1, wherein the size of the inlet orifice can be regulated by engaging the inlet orifice with one or more inserts.

11. The device for biological purposes such as cell culturing, enzymatic reactions or filtering of fluid according to claim 1, wherein the recessed portions comprises a first regulatory mechanism to regulate the size of the outlet opening.

12. The device for biological purposes such as cell culturing, enzymatic reactions or filtering of fluid according to claim 1, wherein the means for rotating is magnetic.

13. The device for biological purposes such as cell culturing, enzymatic reactions or filtering of fluid according to claim 1, wherein the body or the device comprises means for creating an electrical field.

14. The device for biological purposes such as cell culturing, enzymatic reactions or filtering of fluid according to claim 1, wherein the recessed portions comprise means for retaining a scaffold.

15. The device for biological purposes such as cell culturing, enzymatic reactions or filtering of fluid according to claim 1, wherein two or more devices can be stacked with their surfaces essentially parallel, and where the devices are separated by spacers, said spacers are attached to the devices.

16. The device for biological purposes such as cell culturing, enzymatic reactions or filtering of fluid according to claim 1, wherein said inlet orifice comprises a connective means; said connective means connects an external compartment to said inlet orifice; said external compartment comprises an indicator solution with a given concentration of an indicator.

17. The device for biological purposes such as cell culturing, enzymatic reactions or filtering of fluid according to claim 1, wherein said first-wall is partly interrupted.

18. The device for biological purposes such as cell culturing, enzymatic reactions or filtering of fluid according to claim 1, wherein said device further comprises means for delivery of drugs such as means for connecting a dispensing system to at least one small opening, preferably in the second plate; said at least one small opening is in connection with said aperture.

19. The device for biological purposes such as cell culturing, enzymatic reactions or filtering of fluid according to claim 18, wherein said means for delivery of drugs comprises a drug solution embedded in a leaching material; preferably said leaching material is attached on the second plate in connection with said aperture.

20. The device for biological purposes such as cell culturing, enzymatic reactions or filtering of fluid according to claim 1, wherein said one or more recessed portions-is transparent.

21. The device for biological purposes such as cell culturing, enzymatic reactions or filtering of fluid according to claim 1, wherein said first-wall at least partly comprises a porous material.

22. The device for biological purposes such as cell culturing, enzymatic reactions or filtering of fluid according to claim 1, wherein said inlet opening of said external means comprises a second regulatory mechanism to regulate the size of the inlet opening.

23. The device for biological purposes such as cell culturing, enzymatic reactions or filtering of fluid according to claim 1, wherein the outlet channel is conically shaped, where the smallest cross sectional area of the conically shaped outlet channel is in connection with the aperture and where the conical shape of the outlet channel continues in at least a part of the recessed portion and/or said part of the external means;

said part of the recessed portion and/or the external means being in contact with the outlet channel.

24. The device for biological purposes such as cell culturing, enzymatic reactions or filtering of fluid according to claim 1, wherein the recessed portions and/or the external means comprises a first regulatory mechanism to regulate the size of the outlet opening.

25. The device for biological purposes such as cell culturing, enzymatic reactions or filtering of fluid according to claim 1, wherein the recessed portions and/or the external means comprise(s) means for retaining a scaffold.

26. The device for biological purposes such as cell culturing, enzymatic reactions or filtering of fluid according to claim 1, wherein said first and/or said second wall is/are partly interrupted.

27. The device for biological purposes such as cell culturing, enzymatic reactions or filtering of fluid according to claim 1, wherein said recessed portions and/or said external means are transparent.

28. The device for biological purposes such as cell culturing, enzymatic reactions or filtering of fluid according to claim 1, wherein said first and/or second wall at least partly comprises a porous material.

29. A method comprising providing using a device for biological purposes such as cell culturing, enzymatic reactions or filtering of fluid is placed in a liquid medium; said device further comprising:
   a body having a first and a second surface defining a body thickness there between, said surfaces being essentially parallel, and where said body is delimited by a rim;
   an aperture in the center of the body; said aperture being covered at the first and second surface by a first and second plate, where the first and/or second plate comprises an inlet orifice allowing liquid medium into the aperture;
   means for rotating; said means for rotating being arranged in the aperture between the first and the second plate;
   said rim comprises at least one recessed portion; said recessed portion is a cavity in the rim of the body comprising a first outlet orifice allowing the liquid medium to flow out of the body; and a first wall delimiting said recessed portion along said cavity;
   at least one outlet channel connecting the aperture with said at least one recessed portion;
   wherein the device further comprises an external means, where the external means engages with the recessed portions of the body and comprises an inlet opening and a second outlet opening and a fluid connection between said inlet opening and said second outlet opening;
   wherein said external means is a three-dimensionally shaped element delimited by a second wall defining an exterior surface of said external means
   optionally, an external means engages with the recessed portions, said external means comprises an inlet opening and a second outlet opening and a fluid connection between said inlet opening and said second outlet opening; said external means is a three-dimensionally shaped element delimited by a second wall defining an exterior surface of said external means;
   scaffolds are arranged in the recessed portion or in the external means
where liquid medium is pumped into the aperture of the body through the inlet orifice due to the rotation of the means of rotating and pumped through the at least one outlet channel, through and/or around scaffolds at the recessed portion and/or the external means and out through the first and/or second outlet orifice.

30. The method according to claim 29, wherein are seeded in or at the scaffolds before or after the scaffolds are arranged in the recessed portion or the external means.

31. The method according to claim 29, wherein proteins are immobilised on the scaffold, said proteins are able to interact with components of the liquid medium passing through the scaffold.

32. The method according to claim 31, wherein the proteins are enzymes, said enzymes interacting with a substrate molecule, wherein said substrate molecule is a component of the liquid medium passing through and/or around the scaffold comprising the enzymes.

33. The method according to claim 31, wherein the proteins are antibodies, said antibodies interacting with cells, said cells being components of the liquid medium passing through the scaffold comprising the antibodies.

34. The method according to claim 29, wherein the means for rotating comprises a magnet, said magnet being arranged in the aperture and where the magnet is rotated by the means of an external rotational magnetic field from e.g. a magnetic stirrer.

35. The method according to claim 29, wherein a flow rate of the medium pumped through said inlet orifice is measured by the steps of
   attaching an external compartment comprising an indicator solution comprising an indicator with a first concentration, C1, to the connective means at the inlet orifice;
   allowing said indicator solution to be pumped into said aperture and pumped through at least one outlet channel;
   measuring a second concentration, C2, of said indicator in said liquid medium with a given volume, V, after a given time, dt;
   calculating said flow rate, Q, by a formula; said formula is given by $Q = -(C2*V)/((C2-C1)*dt)$.

36. The method according to claim 29, wherein said medium is pumped through the walls of said recesse portions and/or said external means.

37. A use of a device for biological purposes such as cell culturing, enzymatic reactions or filtering of fluid according to claim 1, wherein the device is used for obtaining perfusion flow.

38. The use of a device for biological purposes such as cell culturing, enzymatic reactions or filtering of fluid according to claim 37, wherein the device is used for culturing of cells or purification of cells from liquids.

39. The use of a device for biological purposes such as cell culturing, enzymatic reactions or filtering of fluid according to claim 37, wherein the device is used for the culturing of three-dimensional cultures.

40. The use of a device for biological purposes such as cell culturing, enzymatic reactions or filtering of fluid according to claim 37, wherein the device is used for bulk-treatment of scaffolds.

41. The use of a device for biological purposes such as cell culturing, enzymatic reactions or filtering of fluid according to claim 37, wherein the device is used for enzymatic reactions, where immobilised enzymes act on proteins provided by the liquid medium.

42. The use of a device for biological purposes such as cell culturing, enzymatic reactions or filtering of fluid according to claim 37, wherein shed blood for postoperative autologous transfusion is filtered by flowing through scaffolds.

\* \* \* \* \*